(12) United States Patent
Parihar

(10) Patent No.: US 7,323,004 B2
(45) Date of Patent: Jan. 29, 2008

(54) DEVICE FOR PROVIDING AUTOMATIC STITCHING OF AN INCISION

(75) Inventor: Shailendra K. Parihar, Coopersburg, PA (US)

(73) Assignee: Ethicon, Inc., Somerville, NJ (US)

( * ) Notice: Subject to any disclaimer, the term of this patent is extended or adjusted under 35 U.S.C. 154(b) by 659 days.

(21) Appl. No.: 10/403,132

(22) Filed: Mar. 31, 2003

(65) Prior Publication Data

US 2004/0092965 A1 May 13, 2004

Related U.S. Application Data

(63) Continuation-in-part of application No. 10/261,429, filed on Sep. 30, 2002.

(51) Int. Cl.
*A61M 29/00* (2006.01)
(52) U.S. Cl. ........................................ 606/213; 128/898
(58) Field of Classification Search ................ 606/144, 606/167, 191, 213, 215; 604/93, 164, 17
See application file for complete search history.

(56) References Cited

U.S. PATENT DOCUMENTS

| | | | |
|---|---|---|---|
| 4,344,435 A * | 8/1982 | Aubin | 604/246 |
| 4,423,730 A | 1/1984 | Gabbay | |
| 5,209,737 A | 5/1993 | Ritchart et al. | |
| 5,242,457 A | 9/1993 | Akopov et al. | |
| 5,308,336 A | 5/1994 | Hart et al. | |
| 5,385,553 A | 1/1995 | Hart et al. | |
| 5,810,721 A | 9/1998 | Mueller et al. | |
| 5,829,447 A | 11/1998 | Stevens et al. | |
| 6,010,531 A | 1/2000 | Donlon et al. | |
| 6,079,414 A | 6/2000 | Roth | |
| 6,328,757 B1 | 12/2001 | Matheny | |
| 6,355,050 B1 * | 3/2002 | Andreas et al. | 606/144 |
| 6,443,957 B1 | 9/2002 | Addia | |
| 6,464,707 B1 * | 10/2002 | Bjerken | 606/139 |
| 6,537,290 B2 | 3/2003 | Adams et al. | |
| 6,585,761 B2 * | 7/2003 | Taheri | 623/1.24 |

FOREIGN PATENT DOCUMENTS

EP  1 312 318 A1  5/2003
WO  WO 03/034908 A2  5/2003

* cited by examiner

*Primary Examiner*—Michael J. Hayes
*Assistant Examiner*—Victor X. Nguyen

(57) ABSTRACT

An automatic suturing device including: a body for insertion into an opening in tissue; a plurality of hooks movably disposed in the body between retracted and extended positions; a suture holder having sutures disposed therein, the suture holder having a mechanism for engaging a portion of the hooks when in the retracted position and for attaching the sutures to a portion of the plurality of hooks; and an actuator for actuating the plurality of hooks from the retracted position to the extended position and for embedding the exposed plurality of hooks with the attached sutures into the tissue surrounding the opening.

21 Claims, 21 Drawing Sheets

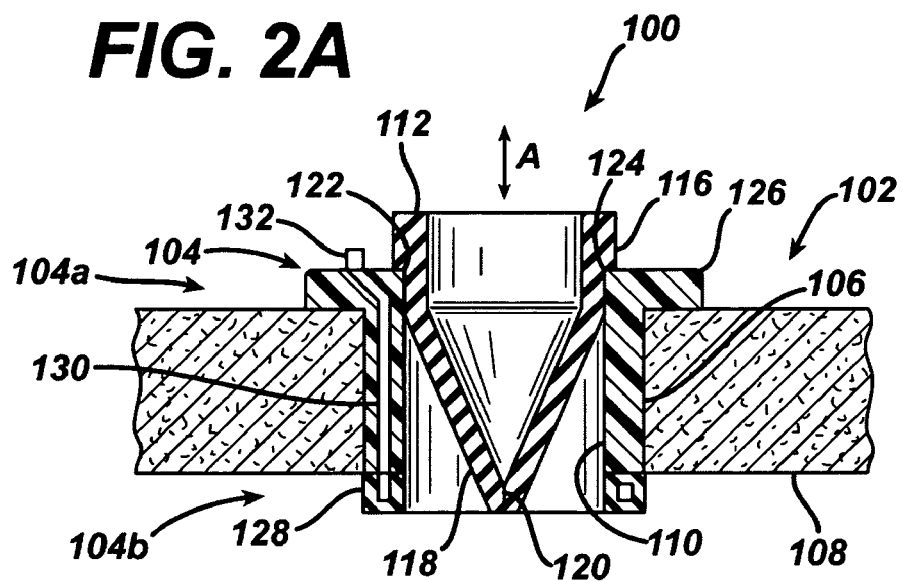
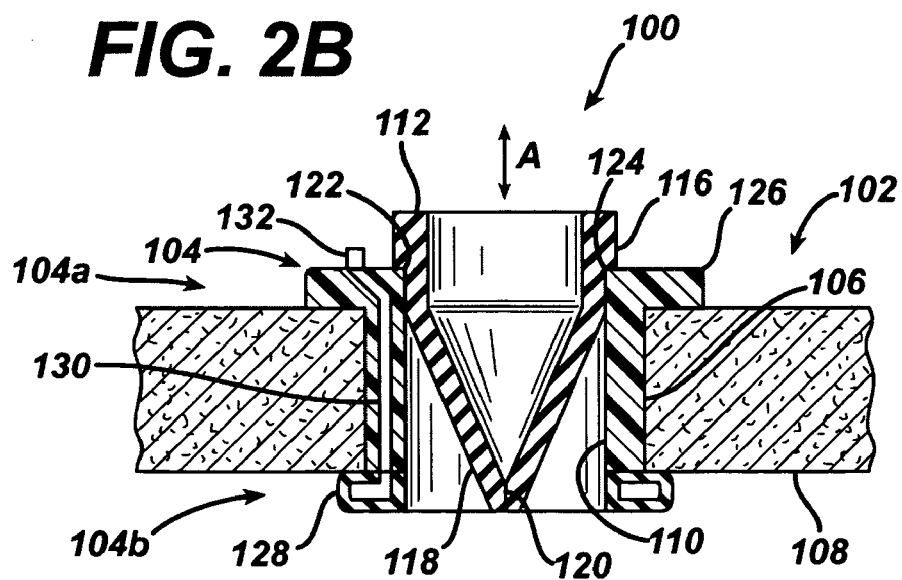

DEVICE FOR PROVIDING AUTOMATIC STITCHING OF AN INCISION

CROSS REFERENCE TO RELATED APPLICATIONS

This application is a Continuation-In-Part of U.S. application Ser. No. 10/261,429, filed Sep. 30, 2002, the entire contents of which is incorporated herein by reference.

BACKGROUND OF THE INVENTION

1. Field of the Invention

The present invention relates generally to a device for providing automatic-stitching of an incision, and more particularly, to a device for providing access to a hollow organ as well as automatic stitching on an incision in the hollow organ.

2. Prior Art

Surgery may be performed using open-chest techniques while the heart is under cardioplegic arrest and circulation is maintained by cardiopulmonary bypass. Using such techniques, a gross thoracotomy is created in order to gain access to the heart and great vessels, facilitating clamping and cannulation of the aorta for inducing cardioplegic arrest, and allowing instruments to be introduced into the chest cavity and into the heart to perform a surgical repair. The necessity of stopping the heart significantly heightens the risks attendant such procedures, particularly the risks of causing ischemic damage to the heart muscle, and of causing stroke or other injury due to circulatory emboli produced by aortic clamping and vascular cannulation.

A number of endovascular approaches for use in procedures in which the heart is arrested have been developed in the prior art. These approaches attempt to allow intracardiac access using catheters introduced transluminally from peripheral vessels into the heart. However, these devices suffer from many problems including a lack of control and precise positionability from the proximal ends of the highly flexible and elongated devices, the significant size constraints of peripheral vessels, and the inability to position the devices in all potentially diseased sites within the heart.

A number of minimally invasive or endoscopic access devices for use in beating heart procedures have also been developed in the prior art. These endoscopic devices are used to gain intracardiac access to the heart. Such devices are disclosed in U.S. Pat. Nos. 6,079,414 to Roth and 5,829,447 to Stevens et al., which are hereby incorporated by reference. However, such devices generally have a substantially long axial bore into which instruments are passed. The long length of the bore restricts the manipulative capability of the instruments passed through the bore into an interior of the heart. For example, a distal end of the instrument mainly moves in an axial direction and cannot stray very much from a central axis in the axial direction. Furthermore, the instruments must be very straight in order to traverse the long length of the bore, thus, curved instruments cannot be utilized with the endoscopic access devices of the prior art. Lastly, because such endoscopic access devices are directed to the heart wall under observation of a viewing device, they cannot be directly secured to the heart wall to maintain a tight seal against blood flow from the heart.

Furthermore, stitching of the incision made to provide access to hollow organs (as well as stitching of wounds and stitching to repair damaged portions of tissue) often require special skills on the part of the surgeon, are not uniform or reliable, and can be time consuming and therefore costly.

SUMMARY OF THE INVENTION

Therefore it is an object of the present invention to provide an access device that overcomes the disadvantages of the prior art.

Accordingly, an automatic suturing device is provided. The automatic suturing device comprising: a body for insertion into an opening in tissue; a plurality of hooks movably disposed in the body between retracted and extended positions; a suture holder having sutures disposed therein, the suture holder having means for engaging a portion of the hooks when in the retracted position and for attaching the sutures to a portion of the plurality of hooks; and actuation means for actuating the plurality of hooks from the retracted position to the extended position and for embedding the exposed plurality of hooks into the tissue surrounding the opening.

Preferably, the device further comprises means for providing access into a hollow organ through the opening. The means for providing access preferably comprises: the body having a bore for passage of at least a distal portion of an instrument into an interior of the hollow organ; and a valve disposed in the bore for allowing passage of the instrument and substantially preventing a fluid in the interior of the hollow organ from leaking outside the hollow organ.

The body preferably comprises first and second body portions movable relative to each other, wherein the actuation means comprises: rotatable actuation means for exposing the plurality of hooks upon rotation of one of the first and second body portions relative to the other of the first or second body portions; and translatable actuation means for embedding the exposed plurality of hooks into the wall upon translation of one of the first and second body portions relative to the other of the first or second body portions. In which case, the automatic suturing device preferably further comprises a fluid seal between the first and second body portions.

Preferably, the suture holder is separately formed from the body and inserted on a distal portion of the body.

In a first version, the means for engaging a portion of the hooks when in the retracted position and for attaching the sutures to a portion of the plurality of hooks comprises an adhering means for adhering the sutures to a portion of the plurality of hooks. Preferably, the adhering means comprises: the suture holder having a longitudinal channel for holding the sutures therein; and the suture holder having two or more collet assemblies each of which correspond to a frayed end of the sutures, each of the collet assemblies having a collapsible collet having a glue chamber containing a dose of glue disposed in an internal channel and means for collapsing the collapsible collet radially into the internal channel; wherein the at least a portion of the plurality of hooks and the frayed ends of the sutures are disposed in the interior channel and wherein each of the collapsible collets are collapsed to compress the frayed ends of the sutures and dose of glue against a portion of the hooks disposed in the interior channel to adhere the sutures to the hooks.

In a second version, the means for engaging a portion of the hooks when in the retracted position and for attaching the sutures to a portion of the plurality of hooks comprises a fastening means for mechanically fastening the sutures to a portion of the plurality of hooks. Preferably, the fastening means comprises: the suture holder having a longitudinal channel for holding the sutures therein; at least a portion of the plurality of hooks having one or more projections; and the suture holder having two or more collet assemblies each of which correspond to a frayed end of the sutures, each of the collet assemblies having a collapsible collet having an internal channel and means for collapsing the collapsible collet radially into the internal channel; wherein the at least a portion of the plurality of hooks and the frayed ends of the sutures are disposed in the interior channel and wherein each of the collapsible collets are collapsed to compress the projections against a corresponding hook to capture the frayed ends of the sutures against a portion of the hooks disposed in the interior channel to fasten the sutures to the hooks.

Also provided is an automatic suturing device comprising: an access device for providing access into a hollow organ during an open surgical procedure, the access device comprising: a body having a distal portion for insertion into an opening in a wall of the hollow organ, the body further having a bore for passage of at least a distal portion of an instrument into an interior of the hollow organ; a valve disposed in the bore for allowing passage of the instrument and substantially preventing a fluid in the interior of the hollow organ from leaking outside the hollow organ; a plurality of hooks movably disposed in the body between retracted and extended positions; and actuation means for actuating the plurality of pins from the retracted position to an extended position and for embedding the exposed plurality of hooks into the wall to secure the body to the wall; and the automatic suturing device further comprises a suture holder having an internal bore disposed on the distal portion of the body, the suture holder having sutures disposed therein and means for engaging a portion of the plurality of hooks when in the retracted position and for attaching the sutures to a portion of the plurality of hooks.

Preferably, the body comprises first and second body portions movable relative to each other and wherein the actuation means comprises: rotatable actuation means for exposing the plurality of hooks upon rotation of one of the first and second body portions relative to the other of the first or second body portions; and translatable actuation means for embedding the exposed plurality of hooks into the wall upon translation of one of the first and second body portions relative to the other of the first or second body portions. In which case, the automatic suturing device preferably further comprises a fluid seal between the first and second body portions.

Preferably, the body has a low-profile length in an axial direction of the bore to increase a manipulative capability of the instrument through the bore. Preferably, the length of the body in the axial direction of the bore is substantially within a range of 1.5 T to 5 T, where T is a thickness of the wall.

In a first version, the means for engaging a portion of the hooks when in the retracted position and for attaching the sutures to a portion of the plurality of hooks comprises an adhering means for adhering the sutures to a portion of the plurality of hooks. Preferably, the adhering means comprises: the suture holder having a first longitudinal channel for holding the sutures therein; the suture holder having a second longitudinal channel for holding a glue therein; and a linking channel for linking at least a portion of the first and second longitudinal channels and corresponding to at least a portion of the plurality of hooks when in the retracted position; wherein the at least a portion of the plurality of hooks are disposed in the linking channel and in communication with both the sutures and glue in the respective first and second longitudinal channels when in the retracted position to adhere at least a portion of a suture to at least a portion of each of the plurality of hooks. Preferably, the suture holder has an internal bore and the first and second longitudinal channels are disposed on an inner surface of the internal bore. Furthermore, the linking channel is preferably disposed on a distal surface of the suture holder.

In a second version, the means for engaging a portion of the hooks when in the retracted position and for attaching the sutures to a portion of the plurality of hooks comprises a fastening means for mechanically fastening the sutures to a portion of the plurality of hooks. Preferably, the fastening means comprises: the suture holder having a longitudinal channel for holding the sutures therein; at least a portion of the plurality of hooks having one or more projections; and the suture holder having two or more collet assemblies each of which correspond to a frayed end of the sutures, each of the collet assemblies having a collapsible collet having an internal channel and means for collapsing the collapsible collet radially into the internal channel; wherein the at least a portion of the plurality of hooks and the frayed ends of the sutures are disposed in the interior channel and wherein each of the collapsible collets are collapsed to compress the projections against a corresponding hook to capture the frayed ends of the sutures against a portion of the hooks disposed in the interior channel to fasten the sutures to the hooks.

Still provided is a method for automatically stitching an opening in tissue. The method comprising: inserting a portion of a device into the opening; extending a plurality of hooks from the device and through the tissue surrounding the opening; inserting at least a portion of each of the plurality of hooks back into the device; attaching the at least a portion of each of the plurality of hooks to a suture; withdrawing the plurality of hooks and attached suture from the tissue surrounding the opening and through the opening; severing the sutures from the at least portion of each of the plurality of hooks; and pulling the sutures to close the opening. The method preferably further comprises tying the sutures together after closing the opening.

The attaching preferably comprises adhering the at least a portion of each of the plurality of hooks to the sutures. Alternatively, the attaching comprises mechanically fastening the at least a portion of each of the plurality of hooks to the sutures.

Still yet provided is a method for providing access into an interior of a hollow organ for manipulation of an instrument therein. The method comprising: providing access to the hollow organ; making an opening in a wall of the hollow organ; inserting a body of an access device in the opening; securing the body to the wall; passing at least a distal portion of an instrument through a bore in the access device to an interior of the hollow organ; substantially preventing a fluid in the interior of the hollow organ from leaking outside the hollow organ; removing the access device from the opening; and automatically closing the hole in the wall of the internal organ upon removal of the access device from the opening.

Preferably, the automatically closing comprises: inserting a portion of the access device into the opening; extending a plurality of hooks from the access device and through the tissue surrounding the opening; inserting at least a portion of each of the plurality of hooks back into the access device; attaching the at least a portion of each of the plurality of hooks to a suture; withdrawing the plurality of hooks and attached suture from the tissue surrounding the opening and through the opening; severing the sutures from the at least portion of each of the plurality of hooks; and pulling the sutures to close the opening. Preferably, the method further comprises tying the sutures together after closing the opening.

BRIEF DESCRIPTION OF THE DRAWINGS

These and other features, aspects, and advantages of the apparatus and methods of the present invention will become better understood with regard to the following description, appended claims, and accompanying drawings where:

FIG. 2A illustrates a sectional view of the intracardiac access device of FIG. 1 as taken along line 2-2 therein in which the access device is inserted into an opening in a heart wall and the expandable balloon is in a relaxed state.

FIG. 2B illustrates the sectional view of FIG. 2A in which the expandable balloon is in an expanded state.

DETAILED DESCRIPTION OF THE PREFERRED EMBODIMENT

Although this invention is applicable to numerous and various types of procedures and providing access to various hollow organs, it has been found particularly useful in the environment of providing intracardiac access in a beating heart open chest procedure. Therefore, without limiting the applicability of the invention to providing intracardiac access in a beating heart open chest procedure, the invention will be described in such environment.

Figure 1:
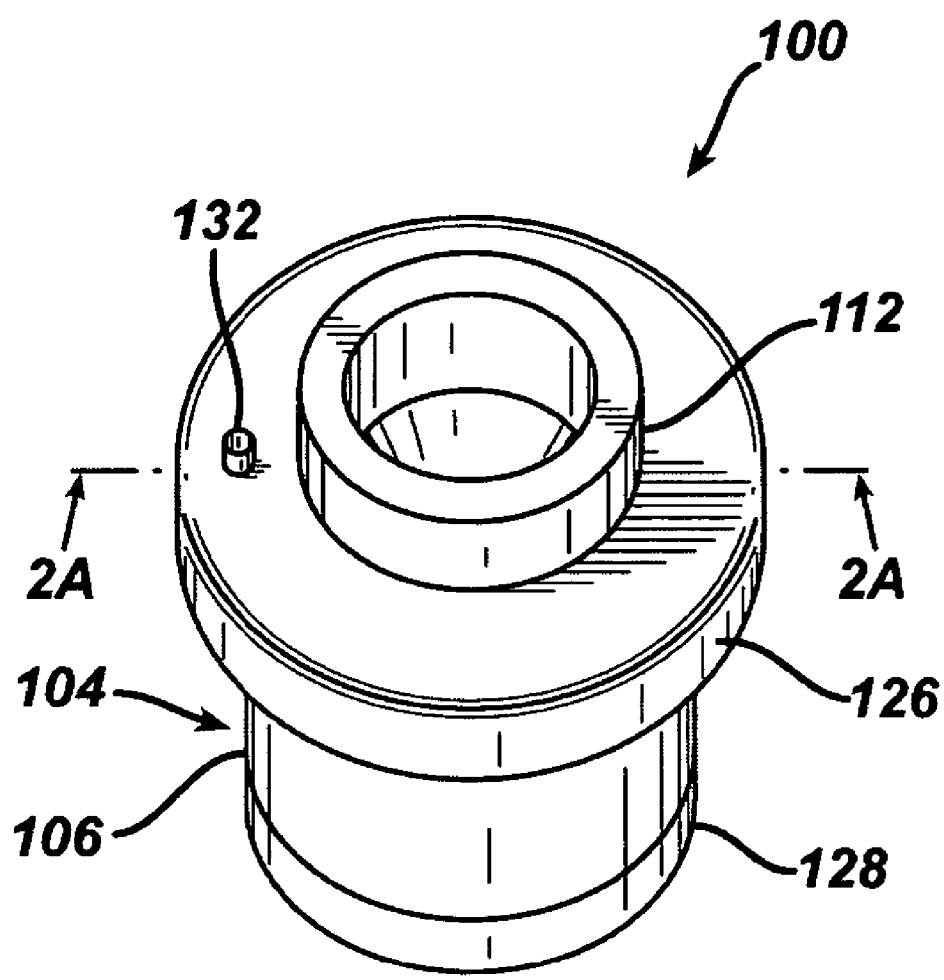
FIG. 1 illustrates an isometric view of a first preferred implementation of an intracardiac access device having an expandable balloon.

Referring now to FIGS. 1, 2A, and 2B there is shown a first preferred implementation of an intracardiac access device having an expandable balloon, the first preferred implementation of the access device being generally referred to by reference numeral 100. The access device 100 provides access into a hollow organ 102, such as the heart, during an open surgical procedure. The access device has a body 104 that is inserted into an opening or incision 106 in a wall 108 of the hollow organ 102. The body 104 is preferably cylindrical in shape and is typically fabricated from a medical grade thermoplastic and can be fabricated from any methods known in the art, such as conventional machining or injection molding. The body 104 has a bore 110 sized to permit at least a distal portion of an instrument (not shown) to pass through the bore 110 and into an interior of the hollow organ 102. The bore extends in an axial direction A from an exterior of the hollow organ 102 to an interior of the hollow organ 102.

A valve 112 is disposed in the bore 110 of the body 104 for allowing passage of the instrument while substantially preventing a fluid in the interior of the hollow organ 102 from leaking outside the hollow organ 102 Preferably, the valve 112 is what is commonly referred to in the art as a duckbill valve. The duckbill valve 112 is fabricated from an elastomer, such as silicone, and has a cylindrical portion 116 and a tapered portion 118. The tapered portion 118 terminates in a slit 120. The slit 120 is normally closed to provide a seal and is configured to conform to a shape of an instrument passed through the slit 120 to provide a seal around the instrument. The duckbill valve 112 further has a stepped portion 122 that rests on a corresponding shoulder 124 of the body 104. The duckbill valve 112 can be press fit into the body or retained therein by way of a medical grade adhesive. Alternatively, a flange (not shown) can be used to capture a portion of the duckbill valve 112. Although, duckbill valves are preferred, other types of valves known in the art can be used without limiting the scope or spirit of the present invention, such as a flexible membrane (not shown) having a small expandable aperture.

The access device 100 also has securing means for securing the body 104 to the wall 108 of the hollow organ 102. The securing means fixes the body 104 to the wall 108 such that it is not in danger of coming off or falling into the interior of the internal organ 102. Preferably, the securing means also provides a seal between the opening 106 and the body 104 of the access device 100. In a first preferred implementation, the securing means comprises a balloon configuration. In such a configuration, a lip 126, which is preferably cylindrical, is disposed on a proximal portion 104a of the body 104. The lip 126 is preferably integrally formed with the body 104, but may also be formed separately and attached to the body 104 by any means known in the art, such as by ultrasonic welding, thermal welding, or with a medical grade adhesive.

A balloon 128 is disposed on a distal portion 104b of the body 104. The balloon is shown in a deflated or relaxed position in FIG. 2A. The relaxed position of the balloon 128 may be due to the lack of a fluid, such as saline or air, therein, or by applying a vacuum to the balloon. A conduit 130 is preferably formed in the body for supplying the fluid from a fluid source (not shown) or applying a vacuum from a vacuum source (not shown) to the balloon for expansion or contraction, respectively, thereof. A port 132 is preferably provided in fluid communication with the conduit 130 to facilitate connection of the fluid or vacuum source to the conduit 130. Preferably, the fluid and vacuum source comprise a syringe (not shown) and the port 132 comprises a self-sealing needle port as is known in the art. FIG. 2B shows the balloon 128 in an expanded position in which the wall 108 of the hollow organ 102 is captured between the lip 126 and the balloon 128. Although not shown, it is preferred that the wall 108 be compressed slightly upon the expansion of the balloon 128.

Figure 3A:
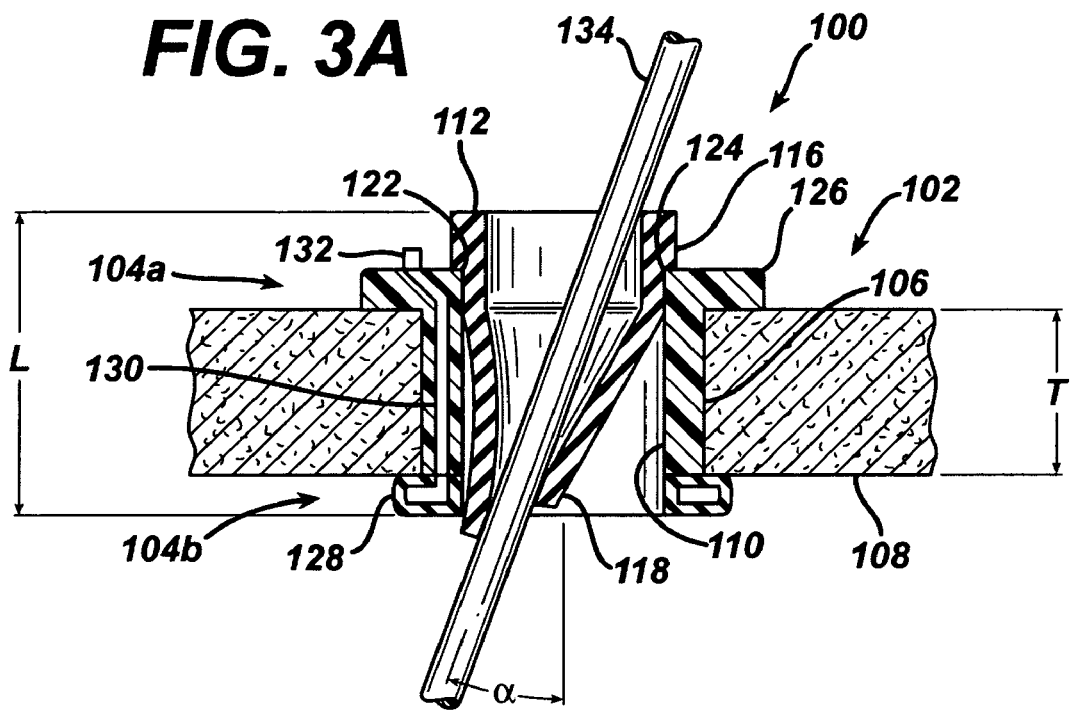
FIG. 3A illustrates the sectional view of FIG. 2B having a straight instrument passed therethrough.
Figure 3B:
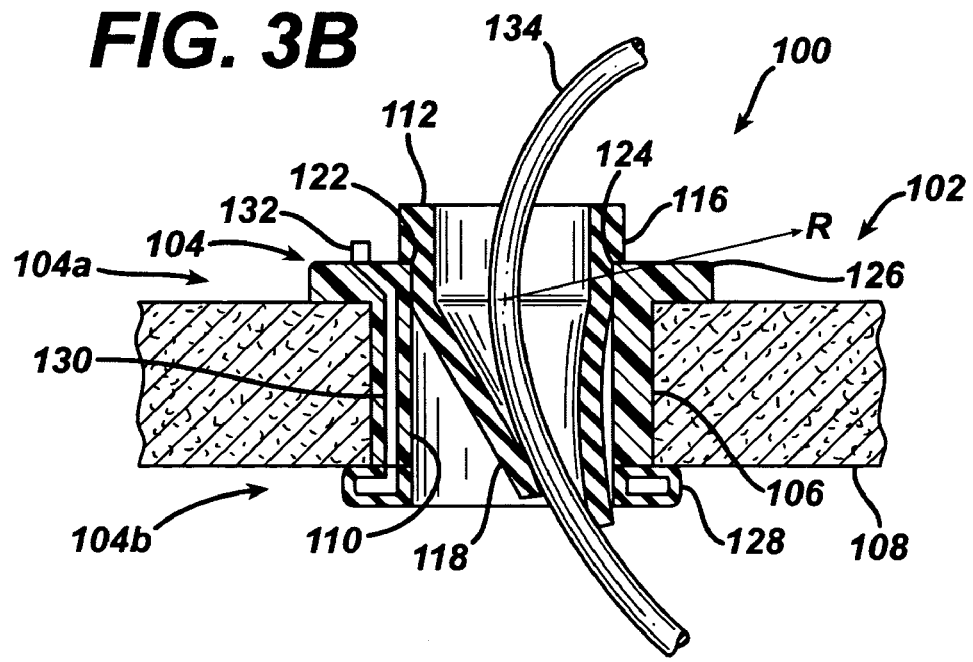
FIG. 3B illustrates the sectional view of FIG. 2B having a curved instrument passed therethrough.

Referring now to FIGS. 3A and 3B, the body 104 has a low-profile length L in the axial direction A of the bore 110 to increase a manipulative capability of the instrument 134 through the bore 110. Preferably, the length L of the body 104 in the axial direction A of the bore 110 is substantially within a range of 1.5 T to 5 T, where T is a thickness of the wall 108. For example, the thickness for a typical heat wall varies between approximately 3-7 mm and the length L of the body 104 is in the range of 4.5 mm to 35 mm, most preferably about 10-15 mm.

As clearly seen in FIG. 3A, the low-profile length L of the body 104 as compared to the thickness T of the wall 108 allows an instrument 134 to be manipulated at a greater angle α with respect to a central axis of the bore than the endoscopic access devices of the prior art. Furthermore, as clearly shown in FIG. 3B, the low-profile length L of the body 104 as compared to the thickness T of the wall 108 allows insertion of a curved instrument having a radius R, which is not possible with the endoscopic access devices of the prior art.

Figure 4:
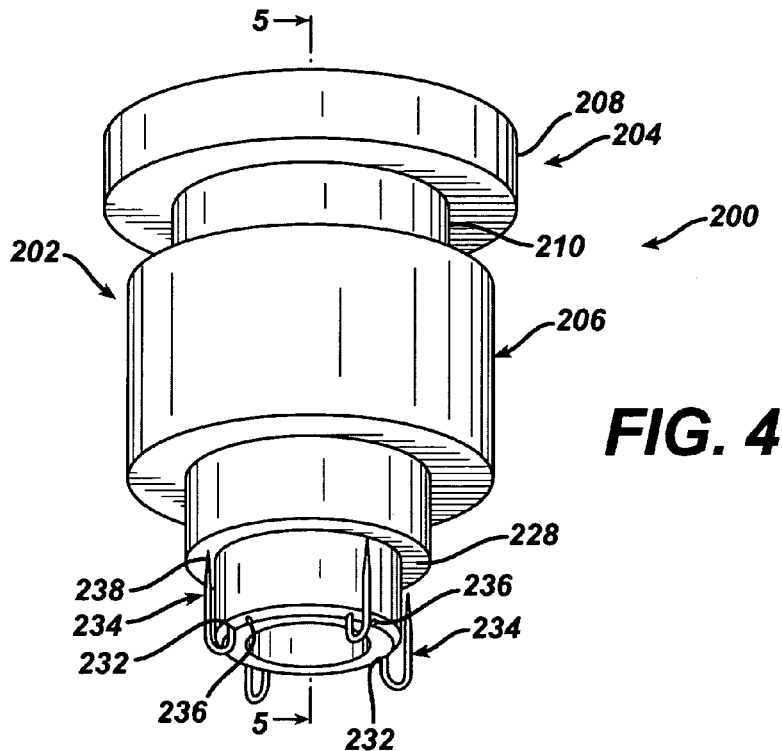
FIG. 4 illustrates an isometric view of a second preferred implementation of an intracardiac access device having a plurality of hooks, the hooks being shown in an exposed position.
Figure 5:
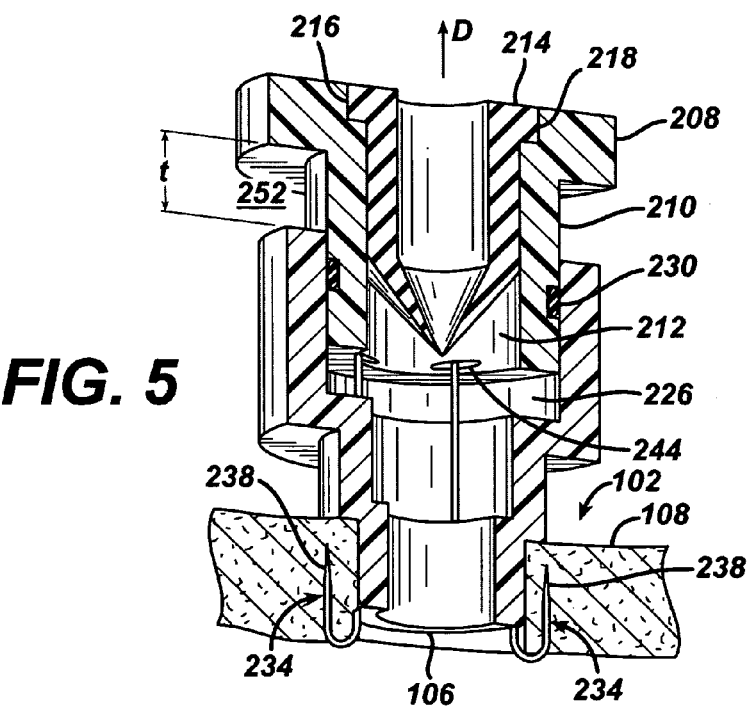
FIG. 5 illustrates a sectional view of the access device of FIG. 4 as taken along line 5-5 in FIG. 4.
Figure 11:
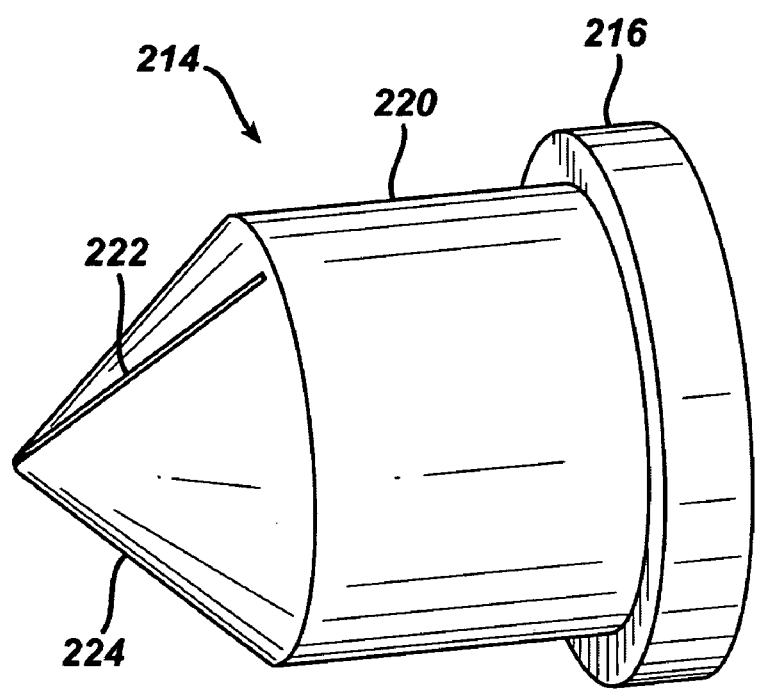
FIG. 11 illustrates a preferred implementation of a valve for use with the access device of FIG. 4.

Referring now to FIGS. 4 and 5, there is illustrated a second preferred implementation of an access device of the present invention, the second preferred access device being generally referred to by reference numeral 200. Access device 200 also preferably has a low-profile shape as discussed above with regard to the first preferred implementation and has the same advantages as discussed above with regard to FIGS. 3A and 3B. Access device 200 includes a body 202 having first and second body portions 204, 206, respectively. The first and second body portions 204, 206 are fabricated from any medical grade material, such as stainless steel or a polymer. The first body portion 204 includes a flange 208 and a cylinder portion 210. The first body portion 204 further has a bore 212 that accommodates a valve 214. Referring now to FIG. 11, the valve 214 is preferably a duckbill or slit valve fabricated from a medically approved elastomer, such as silicone. The valve 214 has a flange 216 which fits within a corresponding stepped groove 218 in the bore 212 of the first body portion 204. The valve 214 also has a cylindrical body portion 220 that fits within the bore 212 of the first body portion 204. The valve 214 has a slit 222 on a conical nose 224 thereof to sealingly accommodate an instrument inserted through the access device 200. The valve 214 is retained in the bore 212 by any means known in the art such as by adhesive or press-fit. The valve 214, although shown disposed in the first body portion 204 may also be disposed in the second body portion 206 and although shown and described as a discrete part may be integrally formed with either of the first and second body portions 204, 206.

Referring back to FIGS. 4 and 5, the second body portion 206 has a bore 226, at least a portion of which accommodates the cylinder portion 210 of the first body portion 204 such that it is free to both rotate and translate within the bore 226 of the second body portion 206. The second body portion 206 further has at least one shoulder or flange 228 on an exterior surface thereof. A seal, such as an o-ring 230 is provided to seal a fluid path between the first and second body portions 204, 206. The second body portion 206 further has a plurality of first longitudinal channels 232 corresponding to each of a plurality of hooks 234 disposed circumferentially about the second body portion 206. Each of the plurality of hooks 234 have at least a portion thereof which is slidingly disposed in a corresponding first longitudinal channel 232. The second body portion also includes a plurality of second longitudinal channels 236 for housing an upturned portion 238 of the hooks 234 when the hooks 234 are in an unexposed position.

Figure 10:
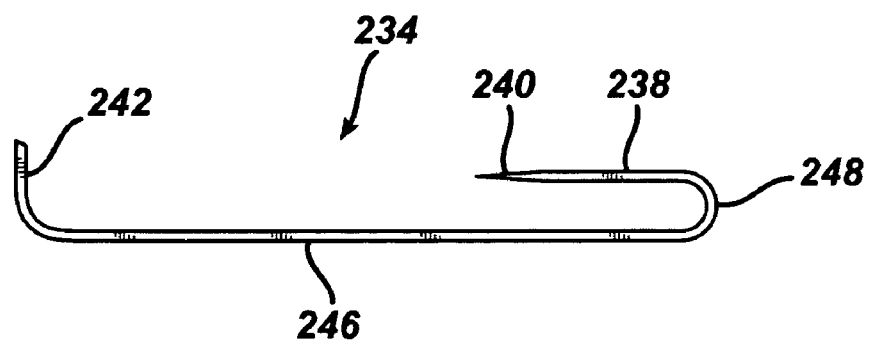
FIG. 10 illustrates a side view of a preferred implementation of one of the plurality of hooks for use with the access device of FIG. 4.

Referring now to FIG. 10, one of the plurality of hooks 234 is shown therein. The hooks 234 are fabricated from a medically approved metallic material, such as stainless steel and have a sharp pointed end 240 at the end of the upturned portion 238. At a proximal end of the hook is a tuned-in portion 242 that engages with and is retained in portions of the first body portion 204, such as in corresponding circumferential slots 244 in the bore 212 of the cylinder portion 210. At the distal end of the hooks 234 is the upturned portion 238. A straight portion 246 connects the in-turned 242 and upturned 238 portions with a curved portion 248 at a transition between the straight portion 246 and the upturned portion 238. At least a portion of the straight portion 246 is slidingly disposed in a corresponding first longitudinal channel 232.

Figure 6:
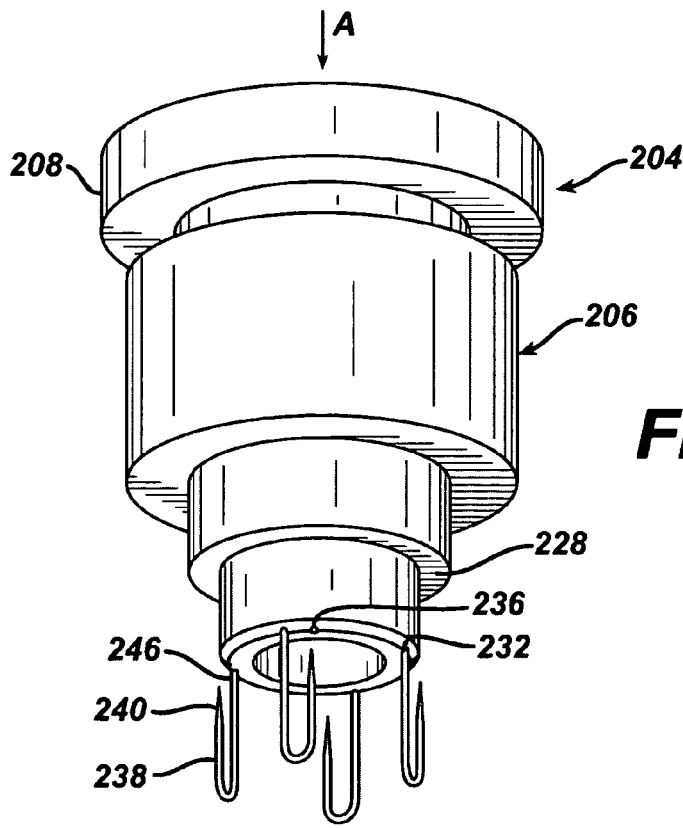
FIG. 6 illustrates an isometric view of the access device of FIG. 6 with the plurality of hooks being rotated while in an extended position.
Figure 7:
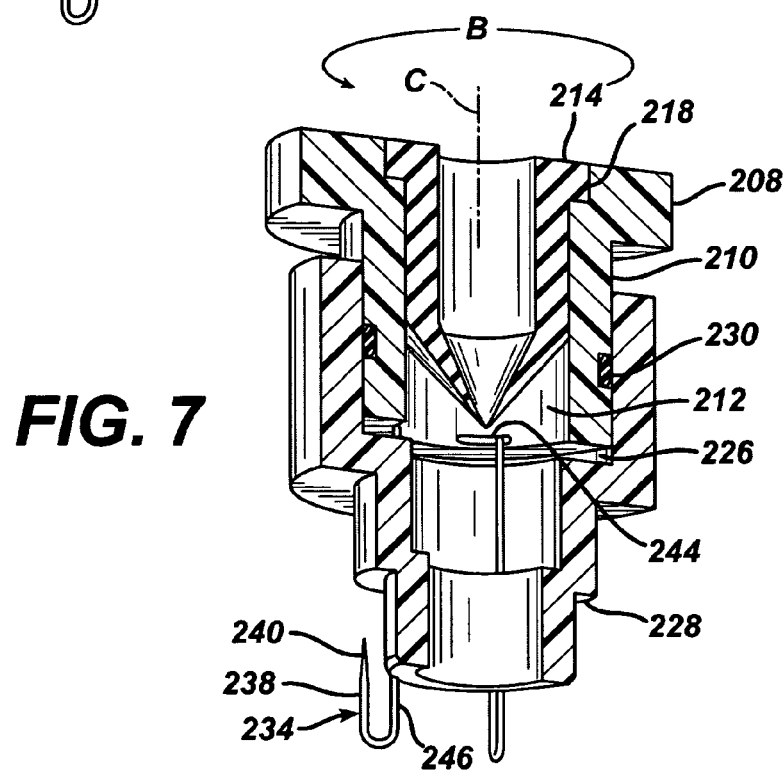
FIG. 7 illustrates a sectional view of the access device of FIG. 4 with the plurality of hooks being in an extended position.
Figure 8:
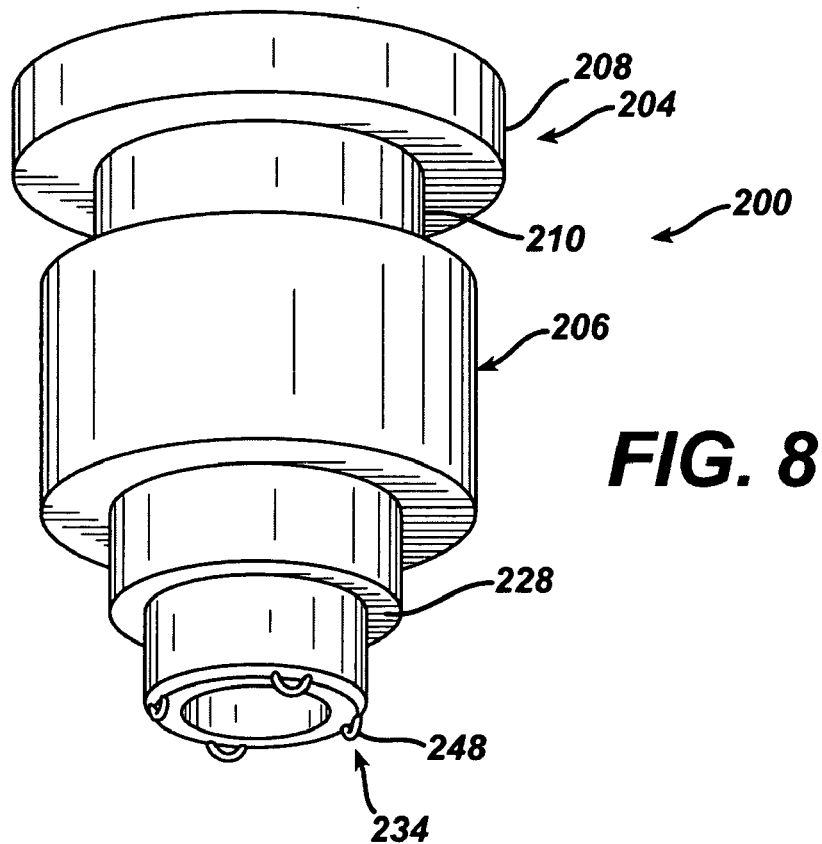
FIG. 8 illustrates an isometric view of the access device of FIG. 7 with the plurality of hooks in the unexposed position.

Referring now to FIGS. 5-8, an operation of the access device 200 of the second preferred implementation will be described. The access device 200 is securely positioned in an incision 106 in a wall 108 of a hollow organ 102, such as the heart. The incision is made by any methods known in the art and may be a slit or a punched hole after access is provided to the hollow organ, such as by a gross thoracotomy. The wall 108 is shown in FIG. 5, but omitted from FIGS. 6-8 for the sake of clarity. Referring first to FIG. 8, the upturned portions 238 of the hooks 234 are disposed in corresponding second longitudinal channels 236 such that the sharp pointed ends 240 are unexposed. The access device is inserted into the incision 106 while the hooks 234 are in the unexposed position as shown in FIG. 8. While the upturned portions 238 are shown as being disposed in the second longitudinal channels 236 in the unexposed position, they can alternatively be disposed in corresponding cut-outs (not shown) on the exterior of the second body portion 206.

Figure 9:
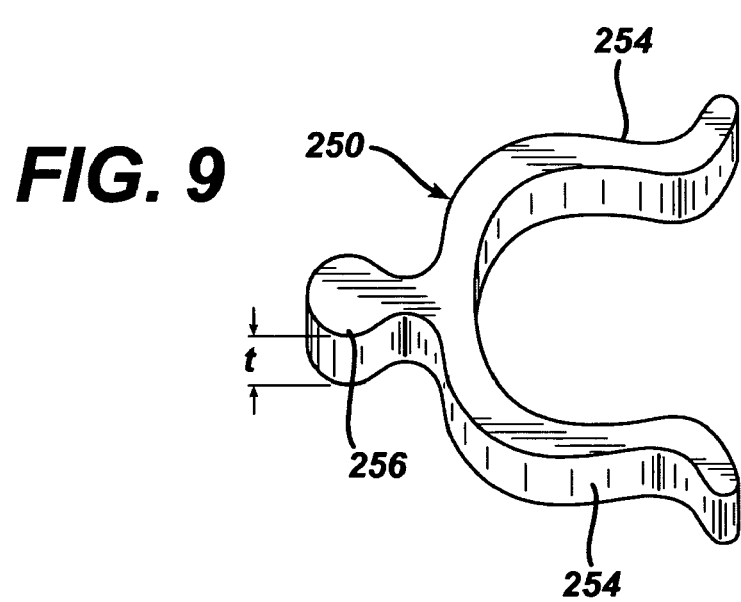
FIG. 9 illustrates an isometric view of a spacer for use with the access device to lock the same with the hooks in the exposed position.

Referring next to FIG. 6, the first body portion 204 is translated relative to the second body portion 206 in the direction of arrow A to extend the upturned portions 238 from the second longitudinal channels 236. Referring now to FIG. 7, the first body portion 204 is then rotated in the direction of arrow B about a central axis C to turn the upturned portions 238 90 degrees and expose the sharp pointed ends 240. When the first body portion 204 is rotated, the hooks 234 are rotated by an interference with the in-turned portions 242 of the hooks 234 and a wall of the corresponding slots 244. Once the hooks 234 are both extended and exposed as shown in FIG. 6, the first body portion 204 is translated in the direction of arrow D (opposite to the direction of arrow A) to embed the upturned portions 238 into the wall 108 of the hollow organ 102 circumferentially about the incision 106, as shown in FIG. 5. The access device 200 is then secured to the wall 108 by sandwiching the wall 302 between the step or flange 228 and the curved portions 248 of the hooks 234. Referring now to FIGS. 5 and 9, while the hooks 234 are embedded into the wall 108, a locking clip 250 is disposed in a gap 252 between the flange 208 of the first body portion 204 and the second body portion 206 to prevent any translation of the first body portion 204 in the direction of arrow A. The thickness t of the locking clip 250 substantially conforms to a thickness t of the clip. The locking clip 250 is preferably fabricated from a medically approved polymer and has fingers 254 which elastically deform to fit within the gap 252. The locking clip 250 further has a pull 256 for facilitating handling and inserting and removing the locking clip 250 into and from the gap 252. Locking clip 250 may have a tether attached to it on one end and to a point outside the operative field on another end to prevent locking clip 250 from inadvertently being left within the patient when the procedure is complete. Alternatively, the locking clip 250 may be tethered to the access device 200 itself. While the access device 200 is secured and locked to the wall 108, surgical instruments (not shown) are inserted through the valve such that the working ends thereof are inserted into an interior of the hollow organ for performing a necessary surgical procedure.

After completion of the surgical procedure, the access device 200 is removed and the incision 106 is closed. To remove the access device 200 from the incision 106, the clip 250 is removed and the first body portion 204 is translated in the direction of arrow A to dislodge the upturned portions 238 of the hooks 234 from the wall 108. The first body portion 204 is then rotated in a direction opposite to that of arrow B about the central axis C to rotate the hooks 90 degrees such that the sharp pointed ends 240 are aligned with the second longitudinal channels 236. The first body portion 204 is then translated in the direction of arrow D to return the up-turned portions 238 of the hooks 234 to the unexposed positions in the second longitudinal channels 236. The access device 200 is then removed from the incision 106 and the incision 106 is closed by any means known in the art, such as with sutures or surgical glue.

Figure 12:
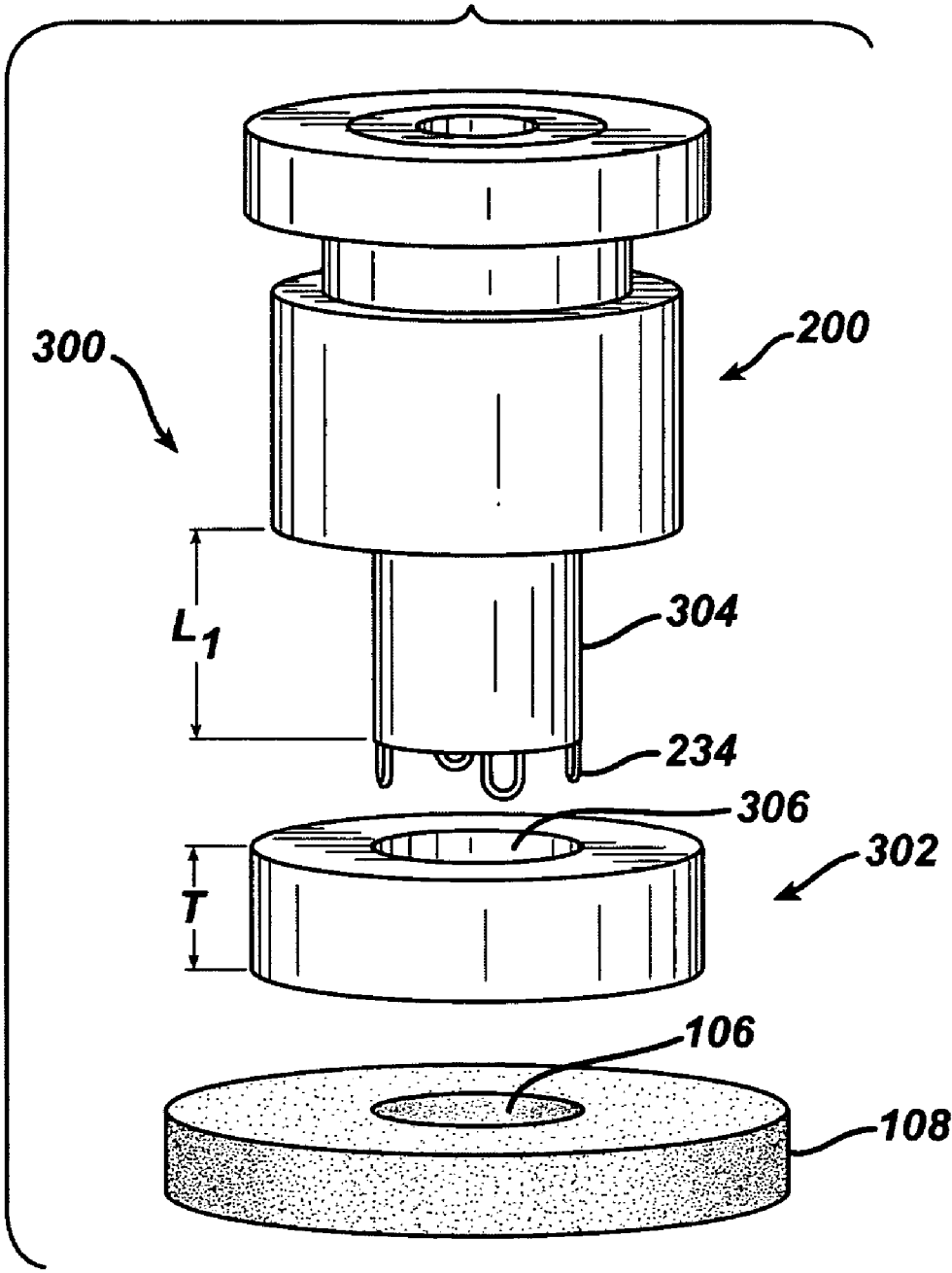
FIG. 12 illustrates a perspective exploded view of the access device substantially similar to that of FIG. 4 used together with a suture holder to provide an automatic stitching of an incision.
Figure 13:
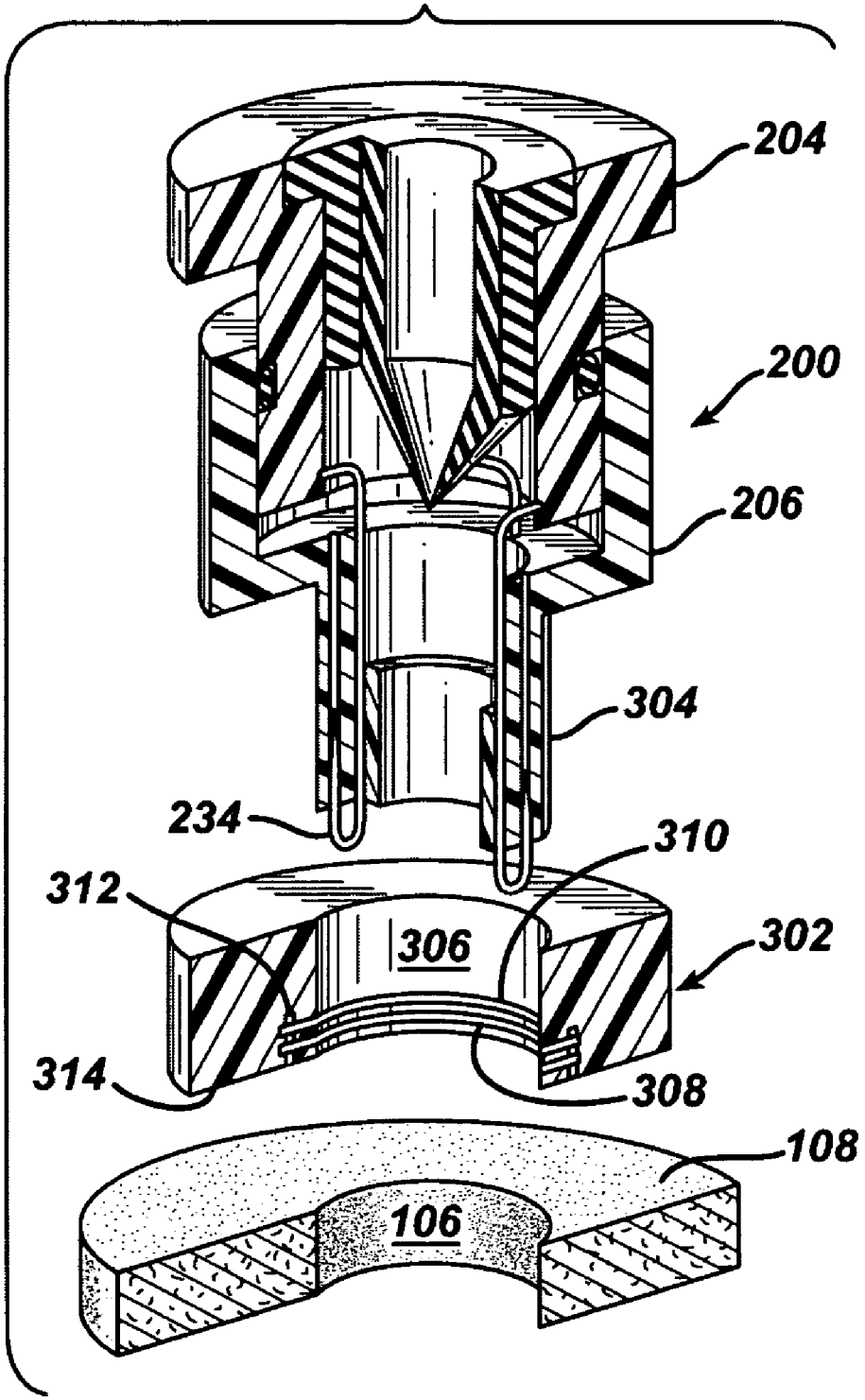
FIG. 13 is a sectional view of the exploded view of the access device and suture holder of FIG. 12.

Referring now to FIGS. 12 and 13 there is illustrated an automatic stitching device, referred to generally by reference numeral 300. Preferably, the automatic stitching device 300 comprises the access device 200 substantially similar to that described above used in combination with a suture holder 302 to provide an automatic stitching capability to the access device 200 for automatically stitching the incision 106 of the hollow organ 102 after completion of a surgical procedure. Although the automatic stitching device 300 is described in combination with the access device 200, those skilled in the art will appreciate that the same can be used without the features of the access device 200 that facilitate use therewith with surgical instruments. For example, the access device 200 can be configured without the bores 212, 226, and/or valve 214. Furthermore, although described as a separate piece, those skilled in the art will appreciate that the suture holder 302 may be integrally formed with the access device 200. Additionally, the incision 106 is described by way of example only as being in the wall 108 of a hollow organ 102 as described above. Those skilled in the art will appreciate that the automatic stitching device can be used to automatically stitch any incision, wound, or damaged tissue, and can also be used to join two tissues together such as an anastomodic device or in a valve repair or replacement. Lastly, the access device 200 is described as having a cylindrical distal portion 304 for insertion into the incision 106, however, those skilled in the art will further appreciate that the distal portion 304 can be provided in many different shapes for use with different shaped incisions. For example, the distal portion 304 may by oval shaped for use with a linear incision.

Figure 14:
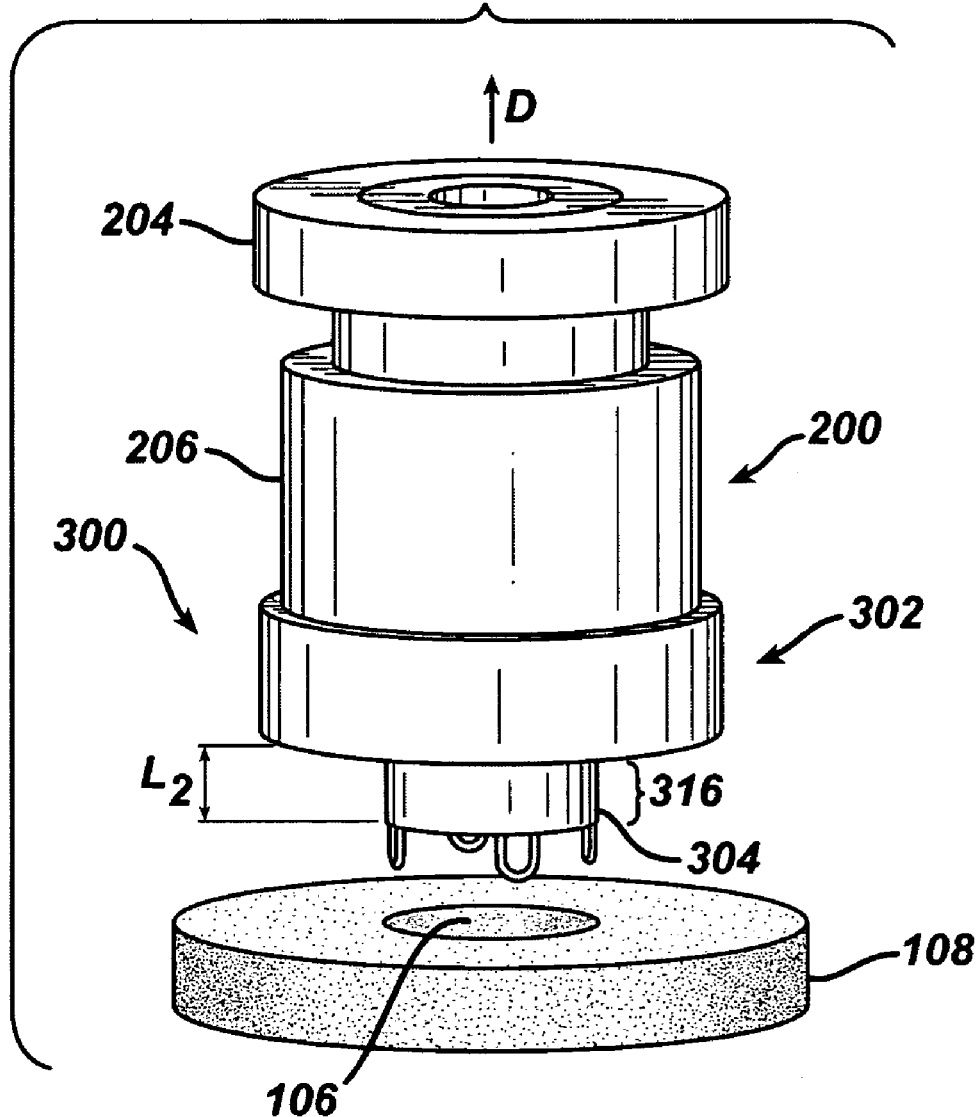
FIG. 14 is a perspective view of the access device and suture holder of FIG. 12 with the suture holder being loaded onto the access device.

The suture holder 302 is preferably disk-shaped and has a bore 306 for acceptance of the distal portion 304 of the access device 200. The suture holder 302 has a thickness T smaller than the length $L_1$ of the distal portion 304 of the access device such that when the suture holder 302 is inserted onto the distal portion 304 of the access device (as shown in FIG. 14), a portion $L_2$ of the distal portion 304 protrudes from the suture holder 302. The suture holder 302 has two internal grooves 308, 310 about a periphery of the bore 306. A proximal one of the internal grooves 310 holds sutures (one each for each of the hooks 234). A distal one of the internal grooves 308 holds a glue for, as will be described below, gluing an end of the suture onto each of the sharp pointed ends 240 of the hooks 234. The glue is preferably a two-part medically approved pressure sensitive high viscosity epoxy wherein each of the two parts are separated in the groove by a membrane. Examples of glues for use with the suture holder 302 are a medical cyanoacrylate glue or Vitralit medical grade adhesive. Alternatively, two grooves can be provided to hold the glue, one for each of the two parts of the epoxy. The suture holder 302 also has a linking groove 312 on a distal surface 314 of the suture holder 302 for accepting the upturned portions 238 of the hooks 234 and for linking the two internal groves 208, 210. Alternatively, the linking groove 312 can be individual holes corresponding to each of the upturned portions 238 of the hooks 234. The suture holder is preferably a disposable device where the glue and sutures are loaded into their respective internal grooves 210, 208 and once used, it is discarded. However, those skilled in the art will appreciate that it can also be reusable where the glue and sutures are loaded into their respective internal grooves 210, 208 prior to each procedure.

Figure 15:
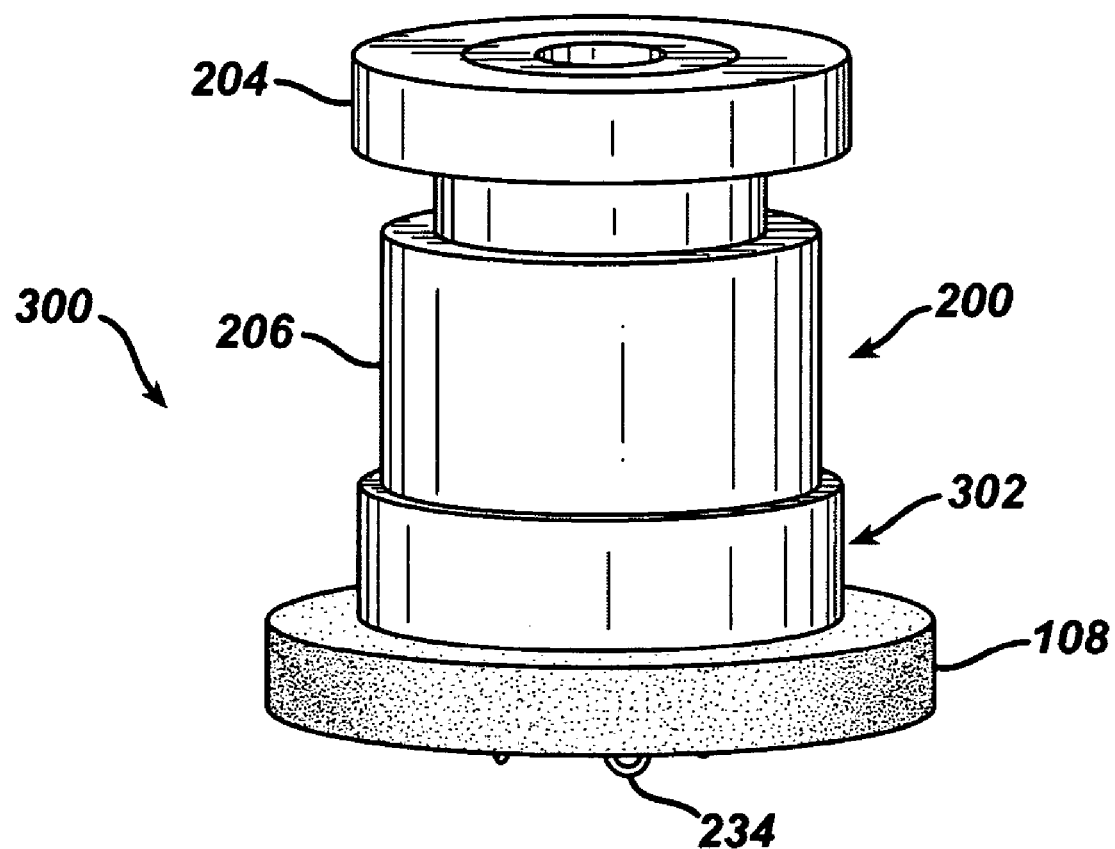
FIG. 15 is a perspective view of the access device and suture holder of FIG. 14 having a distal portion being inserted into an incision in tissue.

Referring now to FIGS. 14-23, the operation of the automatic stitching device 300 will be described. As discussed above, the operation of the automatic stitching device 300 will be described with regard to the access device 200 described above. Referring specifically to FIG. 14, the access device is operated to have the upturned portions 238 of the hooks 234 inserted into their corresponding second longitudinal channels 236, as described above, by rotating the first body portion 204 relative to the second body portion 206 and translating the first body portion 204 relative to the second body portion 206 in the direction of arrow D. The distal portion 304 of the access device 200 is then inserted into the bore 306 of the suture holder 302 such that a portion 316 protrudes therefrom a distance $L_2$. Referring now to FIG. 15, portion 316 is inserted into the incision 106.

Figure 16:
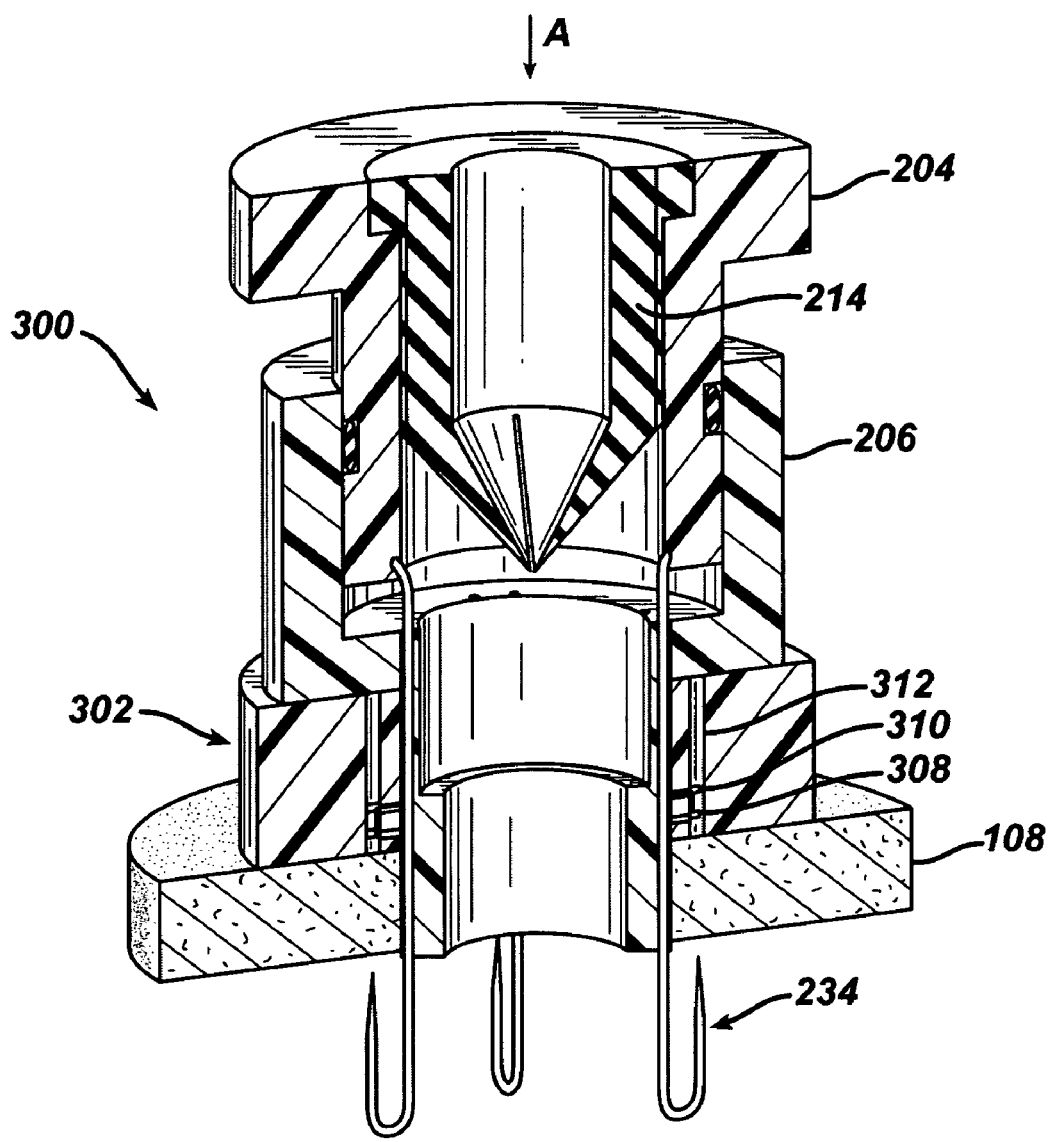
FIG. 16 is a sectional view of the access device and suture holder of FIG. 15 with the hooks in an extended position.
Figure 17:
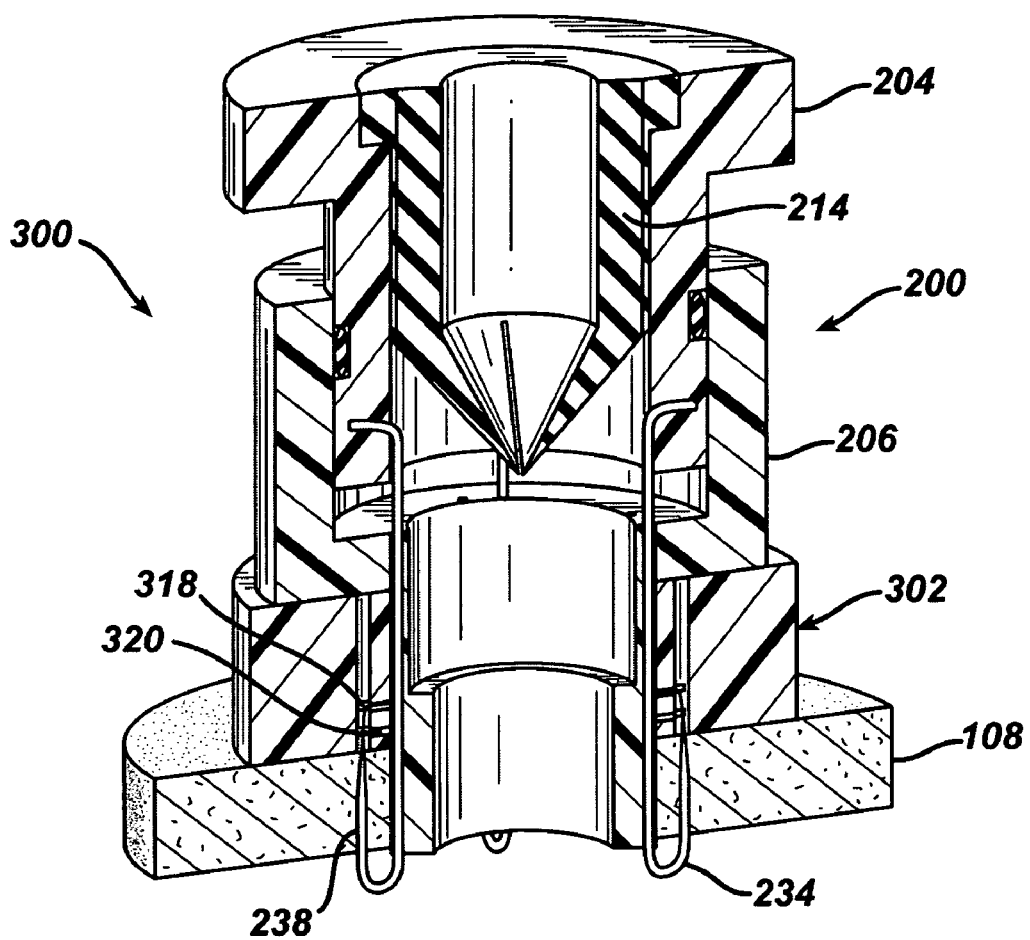
FIG. 17 is a sectional view of the access device and suture holder of FIG. 15 with the hooks retracted into the tissue surrounding the incision and with the sharp pointed ends of the hooks being engaged with the suture holder.

Referring now to FIG. 16, the hooks are then extended, as described above, by translating the first body portion 204 relative to the second body portion 206 in the direction of arrow A. The hooks 234 are further rotated 90 degrees, as described above, by rotating the first body portion 204 relative to the second body portion 206 in the direction of arrow B. As shown in FIG. 17, the hooks 234 are then retracted, as described above, to embed the upturned portions 238 of the hooks 234 in the tissue wall 108 to secure the access device 200 to the tissue wall 108. The access device 200 can then be used, if necessary, in combination with the locking clip 250 to perform a surgical procedure, as described above, by inserting an manipulating surgical instruments through the valve 214 and bores 212, 226.

When the hooks 234 are retracted, each of the sharp pointed ends 240 further enter the linking channel 312 to engage a portion of a suture 318 and glue 320 disposed in the internal grooves 308, 310. If necessary, the sharp pointed ends 240 further puncture the membrane separating the two parts of the epoxy. Thus, while a procedure is being performed, the sutures in one of the internal channels 310 are adhered to each of the sharp pointed ends 240 of the hooks 234. Preferably, a locating means, such as a key (not shown) in the bore 306 and a corresponding keyway (not shown) is provided to orient the suture holder 302 in a predetermined position with respect to the sharp pointed ends 240 of the hooks 234 such that an end of a suture can be located in the linking channel 312 at the location of the sharp pointed ends 240. In this way, the sharp pointed ends 240 would pierce the membrane between parts of the epoxy glue 320 and then contact the suture 318 end to adhere the same to the sharp pointed ends 240 of the hooks 234. Although, the suture holder 302 described above is preferred, those skilled in the art will appreciate that such is given by way of example only and not to limit the scope or spirit of the present invention. Many configurations of the suture holder are possible, such as a disk having sutures with looped ends, where the looped ends correspond to each of a hole or linking channel. In such a configuration, each of the upturned portions 238 of the hooks 234 would have a downwardly facing slit. In operation, on the upstroke through the linking channel, the hooks 234 would displace the loop ends from the hole and pass through the hole, however, on the down stroke, the loop end would be captured in the slit and be retained therein.

Figure 18:
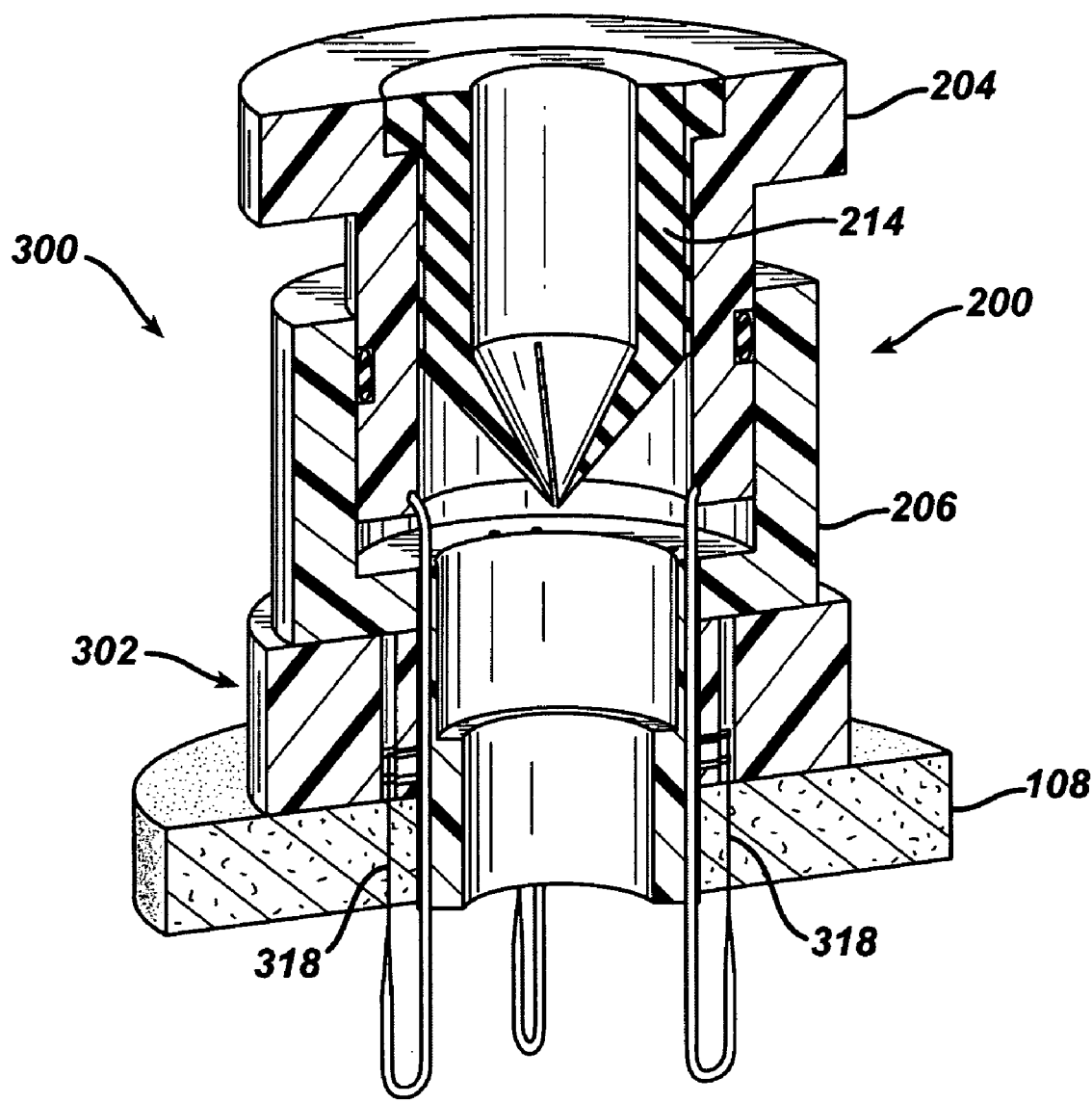
FIG. 18 is a sectional view of the access device and suture holder of FIG. 15 with each of the hooks being in an extended position and having a suture retained thereon.
Figure 19:
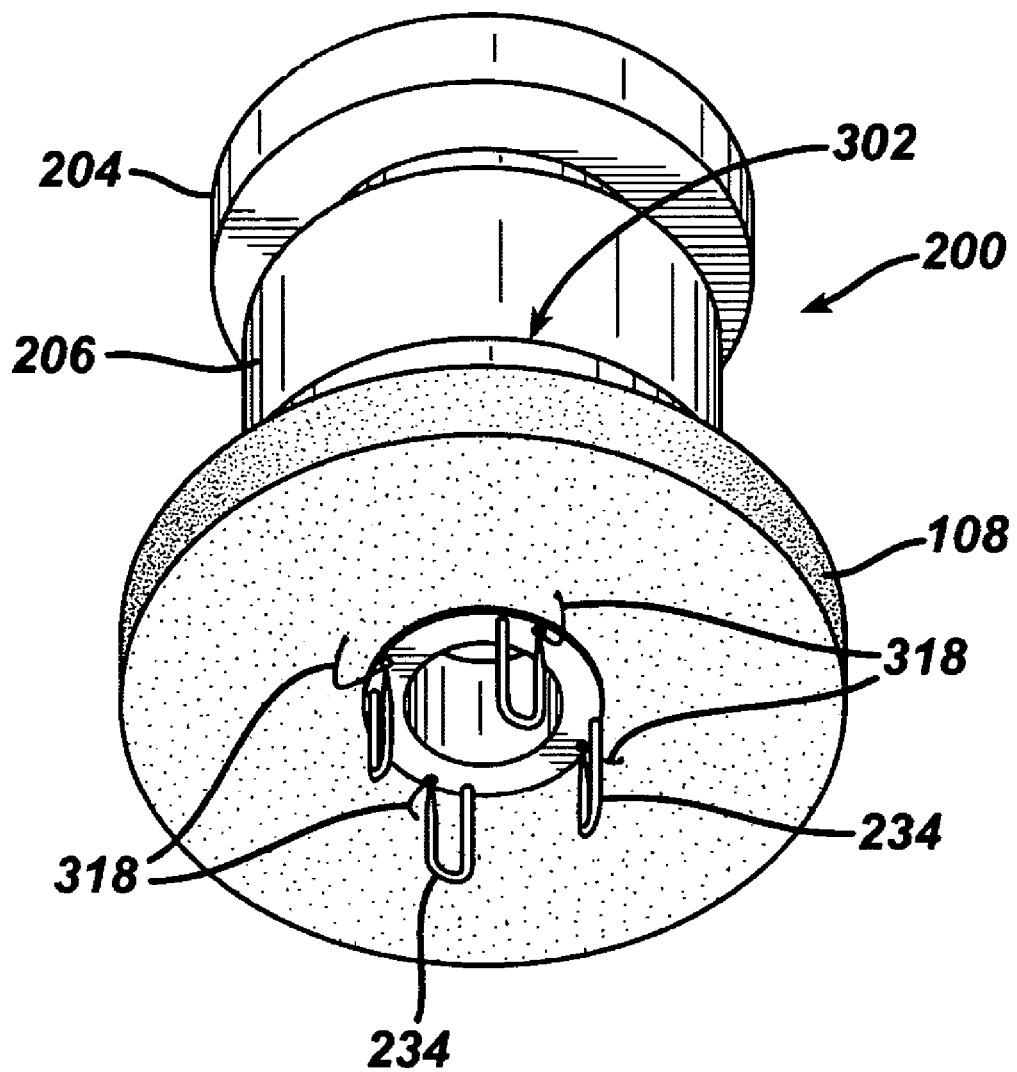
FIG. 19 is a perspective view from the distal end of the access device in which the upturned portions of the hooks having the thread retained thereon are entering their respective second longitudinal channels.
Figure 20:
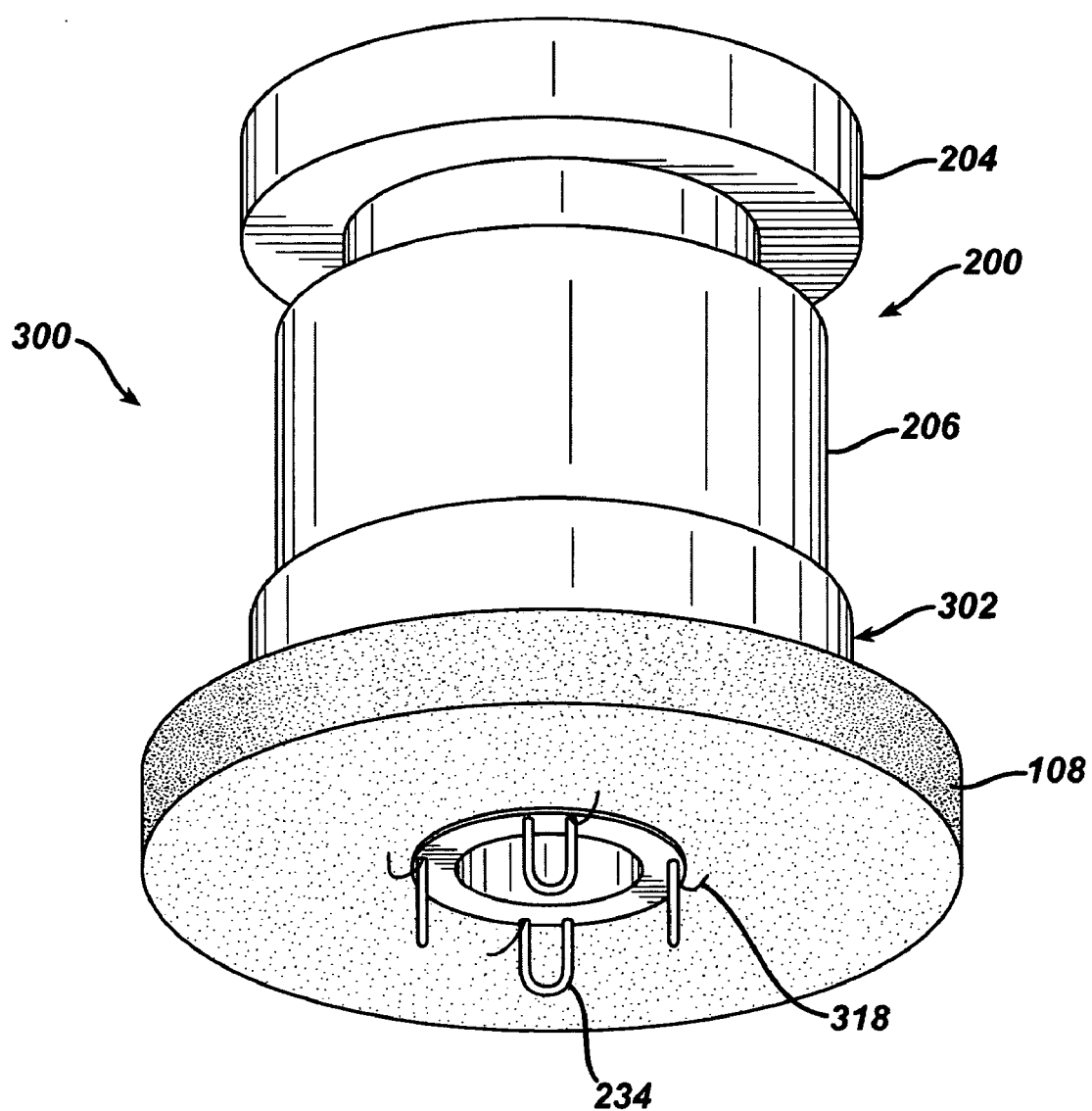
FIG. 20 is a perspective view of the access device and suture holder with the upturned portions of the hooks being entered into the second longitudinal channels.

Referring now to FIG. 18, after the procedure has been completed and/or after the sutures 318 have been retained on each of the hooks 234, the hooks 234 are again extended, as discussed above. As shown in FIG. 18, as the hooks 234 are extended, they withdrawn the suture 318 from the longitudinal channel 310 and pull the sutures 318 through the tissue wall 108 in an area surrounding the incision 106. As shown in FIG. 19, the hooks 234 are rotated 90 degrees, as discussed above, to correspond with their respective second longitudinal channels 236. As shown in FIG. 20, the upturned portions 238 of the hooks 234 are then retracted into the second longitudinal channels 236 along with a corresponding portion of suture 318. It is preferred that the suture 318 be tightly retained in the second longitudinal channels 236, and as such, the second longitudinal channels 236 are sized closely to that of the upturned portions 238.

Figure 21:
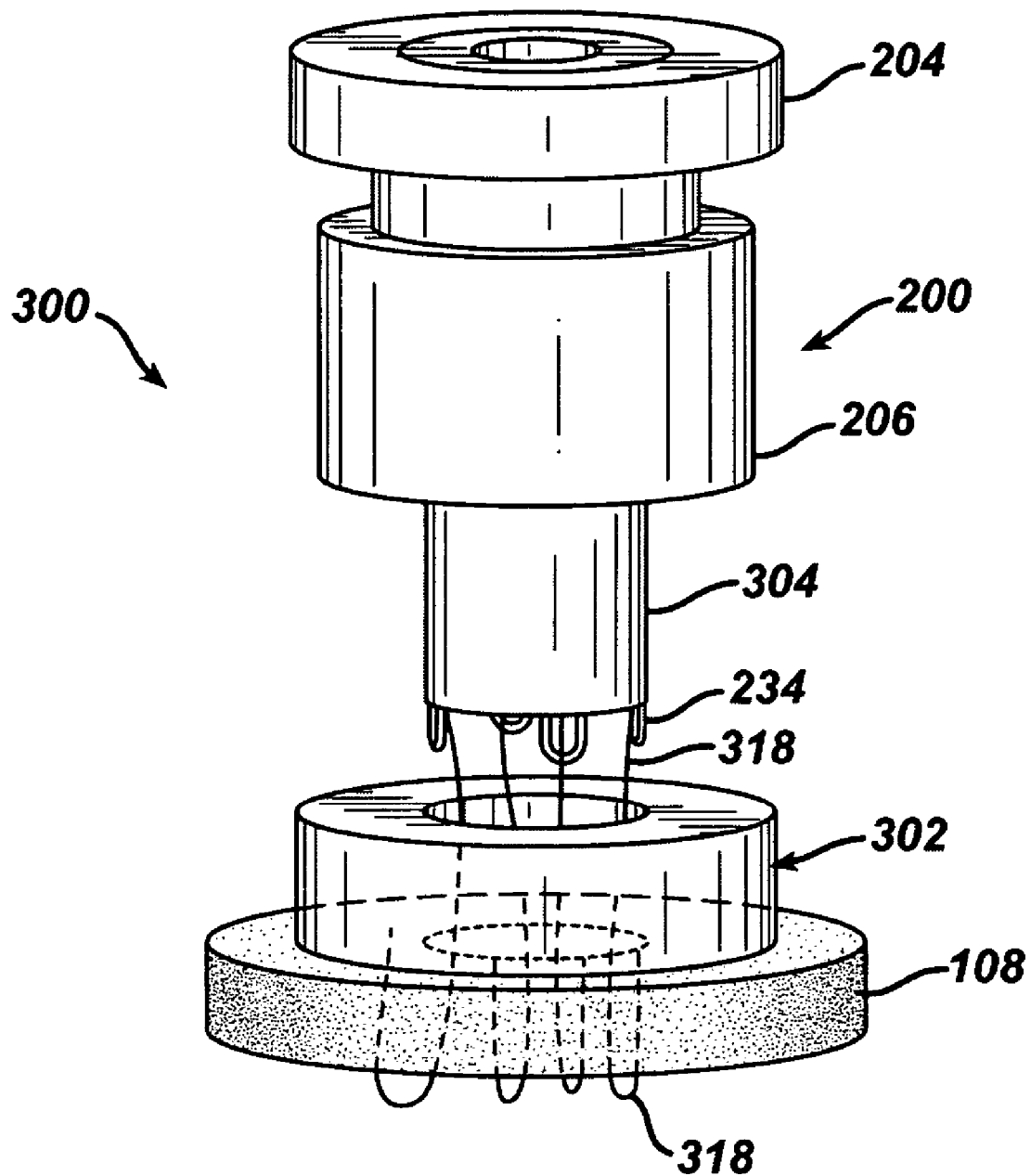
FIG. 21 is a perspective view of the access device and suture holder being removed from the incision.
Figure 22:
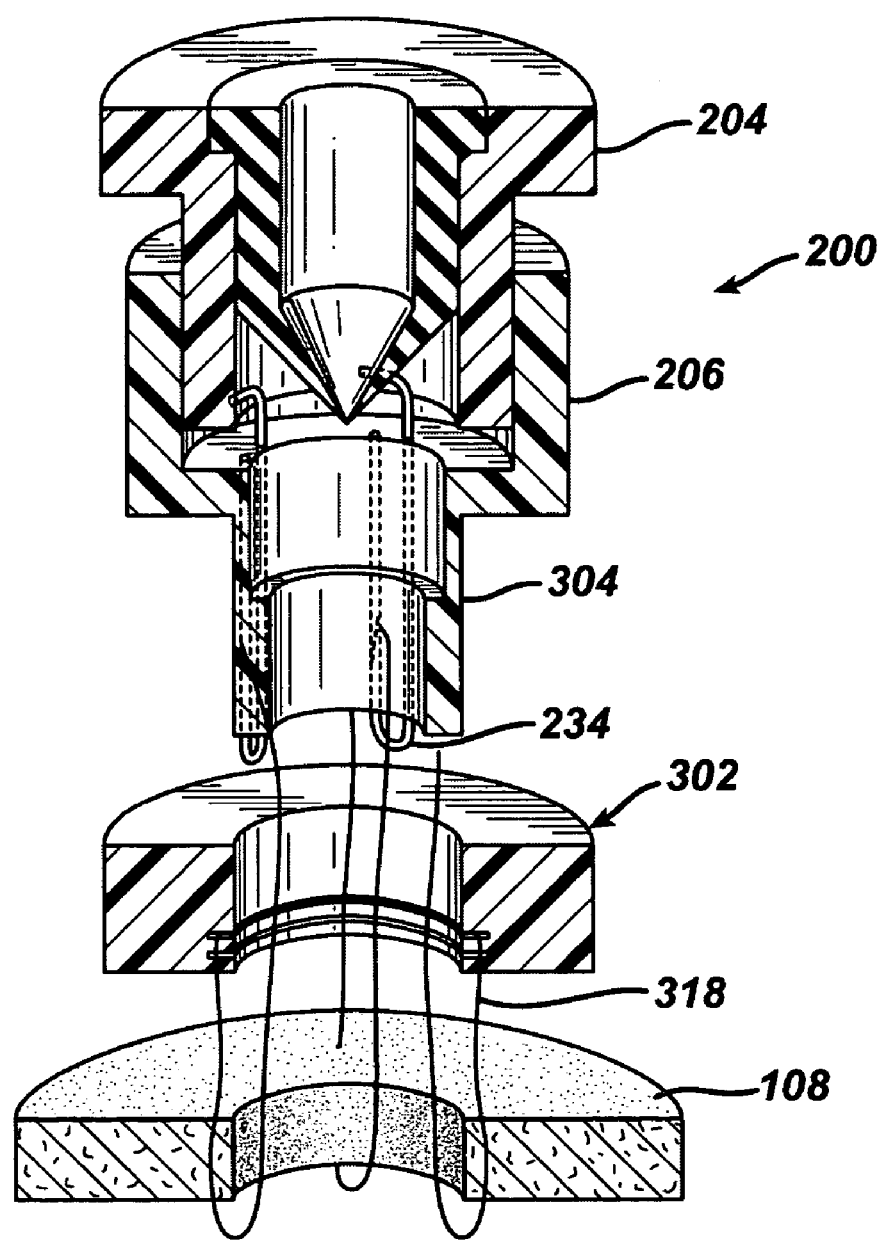
FIG. 22 is a sectional view of the access device and suture holder of FIG. 21.
Figure 23:
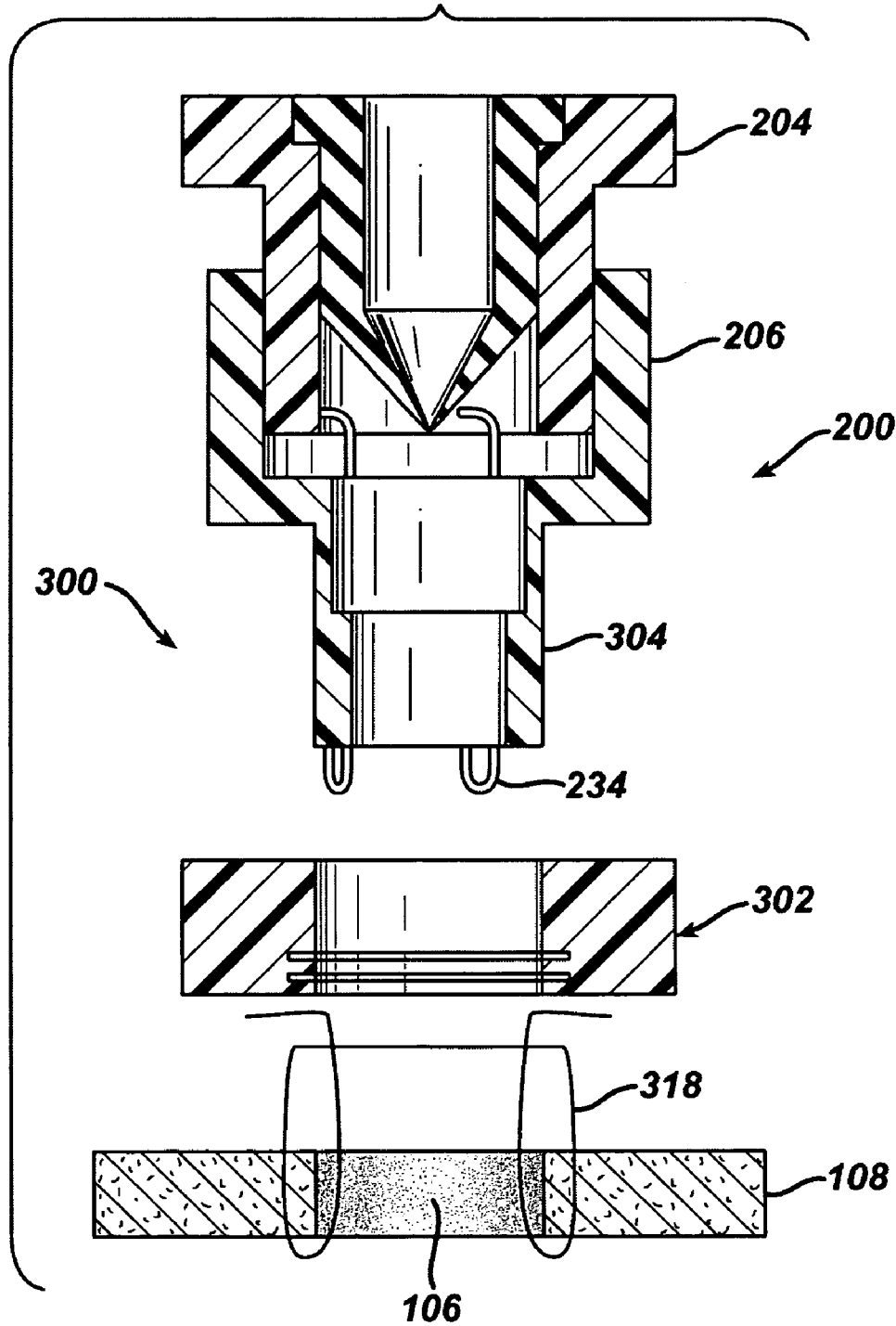
FIG. 23 is a sectional view of the access device and suture holder after the suture holder is separated from the access device and the sutures are separated from the sharp pointed ends of the hooks.

Referring now to FIGS. 21 and 22, the automatic stitching device 300 is then removed from the incision 106 which in turn continues to withdraw suture 318 from the longitudinal channel 310 and the suture holder 302 is removed from the distal portion 304 of the access device 200. As shown in FIG. 23, the sutures 318 are then cut free of the suture holder 302 and/or the access device. At this point, the sutures 318 are looped through the tissue wall 108 surrounding the incision 106 and can be pulled tightly to close the incision 106 and tied. Furthermore, the sutures can alternatively be anchored in the device such that the removal of the device itself pulls the sutures and closes the incision.

Those skilled in the art will appreciate that the preferred implementation of the automatic stitching device 300 described above simplifies the stitching of incisions (or wounds or damaged portions of tissue) and results in a reliable, and uniform stitch that is quickly made and does not require special skills on the part of the surgeon. Furthermore, when used in combination with the access device 200, it provides a single device that provides access, secures to an area surrounding an incision in the tissue, and automatically closes and stitches the incision upon withdrawal of the device. As discussed above, the automatic stitching device 300 can also be used to create an anastomosis between vessels or to repair a damaged heart valve.

Figure 24:
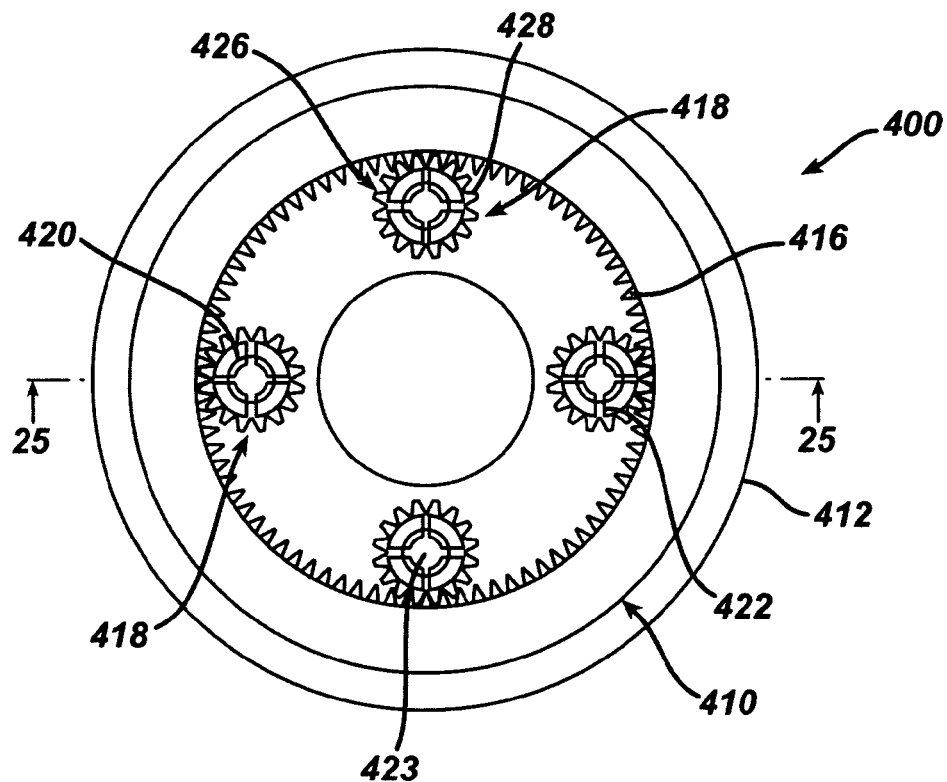
FIG. 24 illustrates a top view of an alternative suture holder of the present invention.
Figure 25:
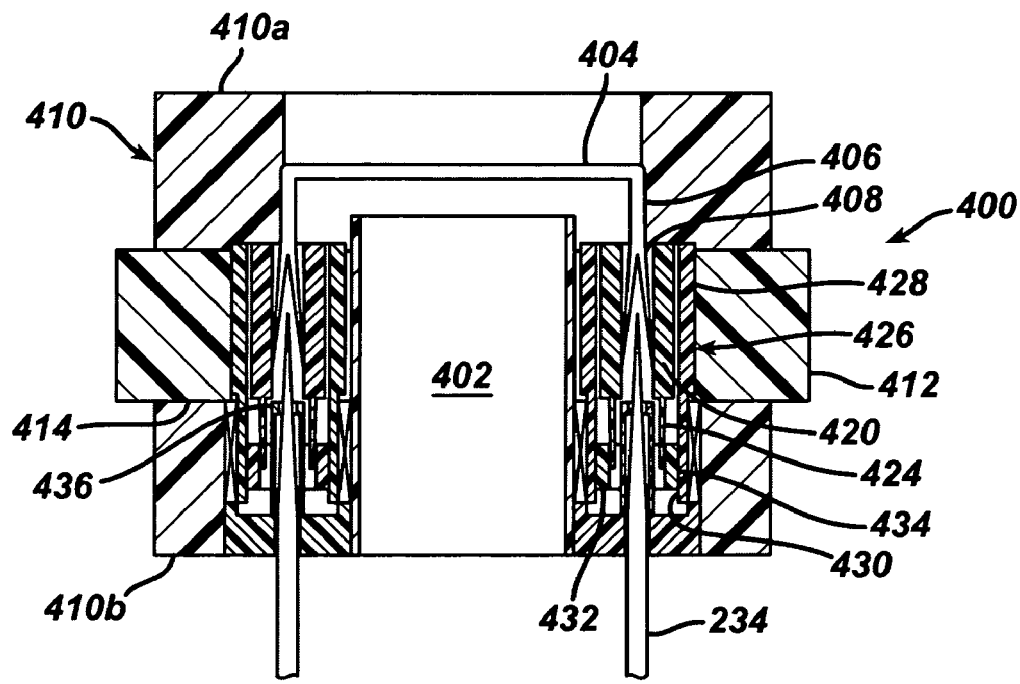
FIG. 25 illustrates a sectional view of FIG. 24 as taken along line 25-25 of FIG. 24, showing the collet assemblies in an open position.
Figure 26:
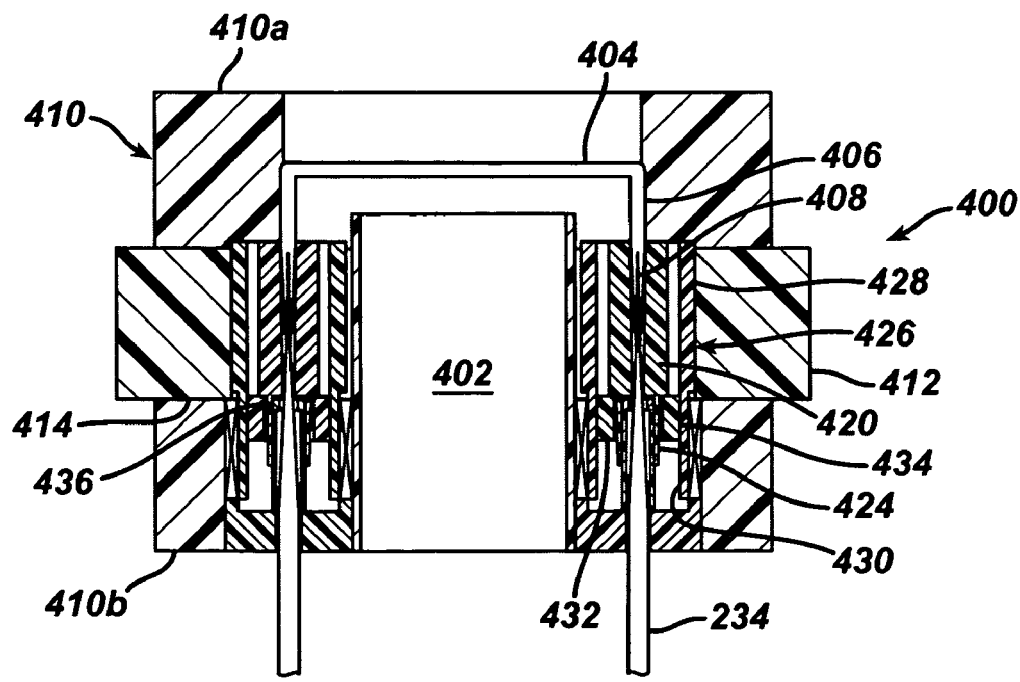
FIG. 26 illustrates the sectional view of FIG. 25 with the collet assemblies in a closed position.

Referring now to FIGS. 24-26 there is illustrated an alternative embodiment of the suture holder of the present invention, the alternative suture holder being referred to by reference numeral 400. Although shown separately for the sake of clarity, the alternative suture holder 400 is intended to be used with the access device 200 substantially as shown and described above with regard to suture holder 302. That is, the distal portion 304 of the access device 300 is disposed in a bore 402 of the alternative suture holder 400 similarly to that described above with regard to suture holder 302. As also discussed above, the access device 300 and suture holder 400 may be integrally formed. The alternative suture holder has a channel 404 for holding one or more sutures 406. The sutures 406 preferably have frayed ends 408 corresponding to the hooks 234 of the access device 300. As discussed above, the alternative suture holder 400 and the access device 300 have locating means, such as a key and corresponding keyway (not shown) for locating the frayed ends 408 of the sutures 406 disposed in the suture holder 400 with the hooks 234 of the access device 300.

The alternative suture holder 400 has a main body portion 410 and an annular ring 412 rotatably disposed in a groove 414 in the main body 410. Preferably the main body 410 has upper and lower halves 410a, 410b, which when assembled, define the groove 414 and allow easy assembly of the ring 412 to the main body 410. The annular ring 412 has a ring gear 416 on an inner surface of the annular ring 412.

The alternative suture holder 400 has a plurality of collet assemblies 418 disposed in a circular pattern about the bore 402. Although four such collet assemblies 418 are shown in FIG. 24, two or more are necessary to perform the auto-stitching of tissue as described above. Each of the collet assemblies 418 includes an inner collet 420 having three or more slits 422 and an internal channel 423 in which is disposed the frayed ends 408 of the sutures 406. A lower portion of the inner collets 420 has a tapered surface 424. The collet assemblies 418 further have an idler 426 having a geared surface 428 meshingly mating with the inner-geared surface of the ring gear 416 and an inner threaded surface 430. A sliding nut 432 is disposed in each of the collet assemblies 418 and having an inner bore disposed over the tapered surface 424. The sliding nut 432 has an outer threaded surface 434 in mating relationship with the inner threaded surface 430 of the idler 426. Finally, each collet assembly 418 has a glue chamber 436 disposed in the internal channel 423. The glue chambers 436 each have a dose of glue, as described above, disposed within a cavity in the chamber 436.

Similarly to that described above with regard to the access device 300 and suture holder 302, the access device 300 is disposed in the bore 402 of the alternative suture holder 400 and the distal portion 304 of the access device 300 is inserted into an incision or other opening in tissue to be sutured. The hooks 234 are deployed from the access device 300, pierce the tissue, and are accommodated in the internal channels 423. As discussed above, the locating means (not shown) preferably locates each of the hooks 234 to correspond with one of the collet assemblies 418, although more hooks 234 can be provided which do not correspond to collet assemblies 418 or additional collet assemblies 418 can be provided for each of the additional hooks 234.

As the hooks 234 penetrate the internal channels 423 of the collet assemblies 418, the sharp pointed ends 240 of the hooks pierce the glue chambers 436 to coat the sharp pointed ends 240 of the hooks 234 with a dose of glue. At this point, the inner bore of the sliding nuts 432 are engaged with a lowered end of the tapered surface 424 of the inner collets 420 as is shown in FIG. 25. The annular ring 412 is then rotated which in turn rotates the idlers 426 meshingly mated thereto by way of the ring gear 416 and geared surface 428. As the idlers 426 rotate, the sliding nuts 432 move upward such that their inner bores further engage and push a corresponding tapered surface 424 due to the engagement of the inner threaded surface 430 of the idler and the outer threaded surface 434 of the sliding nuts 432. As the inner bores of the sliding nuts 432 engage the tapered surface 424 the inner collets 420 close about the slits 422 to compress the frayed ends 408 of the sutures 406 against the sharp pointed ends 240 of the hooks 234 and the glue disposed thereon as shown in FIG. 26. After the glue has dried, thus adhering the sutures 406 to the hooks 234, the access device is removed and the tissue opening is sutured as described above.

Alternatively, the frayed ends 408 of the sutures 406 can be pre-coated with pressure sensitive glue, eliminating the need for a glue chamber 436. In such an alternative configuration, the radial pressure from the collet assemblies 418 will serve to attach the suture 406 to the hook 234.

Figure 27A:
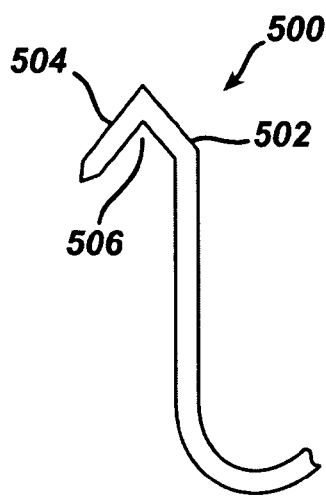
FIGS. 27a and 27b illustrate alternative hooks for use with the alternative suture holder of FIG. 24.
Figure 27B:
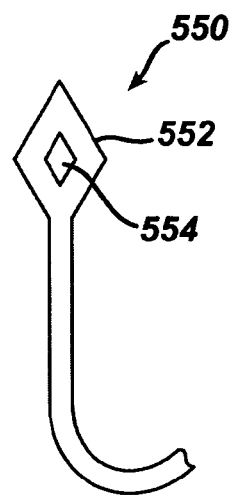

Referring now to FIGS. 27a and 27b, there are shown alternative hooks, referred to generally by reference numerals 500 and 550, respectively. The alternative hooks 500, 550 are similarly configured to the hooks described above with the exception of the sharp pointed ends 502, 552 which are illustrated in FIGS. 27a and 27b, respectively. The sharp pointed ends 502, 552 include means for mechanically capturing and swaging the suture 406 to the hook 500, 550. The alternative hooks 500, 550 can be used together with the alternative suture holder 400 to swage the frayed ends 408 of the suture 406 to the sharp pointed ends 502, 552 of the hooks 500, 550.

The alternative hooks 500, 550 replace the hooks 234 in the access device 300 and are used as described above to pierce the tissue surrounding a tissue opening and which are accommodated in the internal channels 423 of the collet assemblies 418. However, as the annular ring 412 is rotated, the collet assemblies 418 act to mechanically compress the sharp pointed ends 502, 552 of the hooks 500, 550 to thereby capture the frayed ends 408 of the suture 406. In the first alternative configuration, shown in FIG. 27a, the sharp pointed end 502 includes at least one projection 504 forming an opening 506. As the collet assemblies 418 compress the projection, the suture 406 or frayed ends 408 thereof, are captured between the projections 504 and the sharp pointed ends 502 of the hook 500 in the opening 506, thereby swaging the suture 406 to the hook 500 to provide a mechanical bond between the sutures 406 and hook 500. In the second alternative configuration, shown in FIG. 27b, an opening 554 is formed in the sharp pointed end 552, preferably in the shape of a diamond. As the collet assemblies 418 compress the diamond shaped sharp pointed end 552, the suture 406 or frayed ends 408 thereof, are captured in the opening 554, thereby swaging the suture 406 to the hook 550 to provide a mechanical bond between the sutures 406 and hook 550.

The glue chamber 436 may also be used with the alternative hooks 500, 550 to both glue and swage the frayed ends 408 of the sutures 406 to the sharp pointed ends 502, 552 of the hooks 500, 550.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An automatic suturing device comprising:
a body for insertion into an opening in tissue;
a plurality of hooks movably disposed in the body between retracted and extended positions;
a suture holder having sutures disposed therein, the suture holder having means for engaging a portion of the hooks when in the retracted position and for attaching the sutures to a portion of the plurality of hooks; and
actuation means for actuating the plurality of hooks from the retracted position to the extended position and for embedding each of the exposed plurality of hooks into the tissue surrounding the opening, the embedding of each hook occurring first by linear extension of each hook into the tissue, and secondly by rotation and retraction thereof, each hook to return into the tissue,
wherein the means for engaging a portion of the hooks when in the retracted position and for attaching the sutures to a portion of the plurality of hooks comprises:
the suture holder having a first longitudinal channel for holding the sutures therein;
the suture holder having a second longitudinal channel for holding a glue therein; and
a linking channel for linking at least a portion of the first and second longitudinal channels and corresponding to at least a portion of the plurality of hooks when in the retracted position;
wherein the at least a portion of the plurality of hooks are disposed in the linking channel and in communication with both the sutures and glue in the respective first and second longitudinal channels when in the retracted position to adhere at least a portion of a suture to at least a portion of each of the plurality of hooks.

2. The automatic suturing device of claim 1, wherein the device further comprises means for providing access into a hollow organ through the opening.

3. The automatic suturing device of claim 2, wherein the means for providing access comprises:
the body having a bore for passage of at least a distal portion of an instrument into an interior of the hollow organ; and
a valve disposed in the bore for allowing passage of the instrument and substantially preventing a fluid in the interior of the hollow organ from leaking outside the hollow organ.

4. The automatic suturing device of claim 1, wherein the body comprises first and second body portions movable relative to each other and wherein the actuation means comprises:
rotatable actuation means for exposing the plurality of hooks upon rotation of one of the first and second body portions relative to the other of the first or second body portions; and
translatable actuation means for embedding the exposed plurality of hooks into the wall upon translation of one of the first and second body portions relative to the other of the first or second body portions.

5. The automatic suturing device of claim 4, further comprising a fluid seal between the first and second body portions.

6. The automatic suturing device of claim 1, wherein the suture holder is separately formed from the body and inserted on a distal portion of the body.

7. The automatic suturing device of claim 1, wherein suture holder has an internal bore and the first and second longitudinal channels are disposed on an inner surface of the internal bore.

8. The automatic suturing device of claim 1, wherein the linking channel is disposed on a distal surface of the suture holder.

9. An automatic suturing device comprising:
an access device for providing access into a hollow organ during an open surgical procedure, the access device comprising:
a body having a distal portion for insertion into an opening in a wall of the hollow organ, the body further having a bore for passage of at least a distal portion of an instrument into an interior of the hollow organ;
a valve disposed in the bore for allowing passage of the instrument and substantially preventing a fluid in the interior of the hollow organ from leaking outside the hollow organ;
a plurality of hooks movably disposed in the body between retracted and extended positions; and
actuation means for actuating the plurality of pins from the retracted position to an extended position and for embedding the exposed plurality of hooks into the wall to secure the body to the wall; and
a suture holder having an internal bore disposed on the distal portion of the body, the suture holder having sutures disposed therein and means for engaging a portion of the plurality of hooks when in the retracted position and for attaching the sutures to a portion of the plurality of hooks.

10. The automatic suturing device of claim 9, wherein the body comprises first and second body portions movable relative to each other and wherein the actuation means comprises:
rotatable actuation means for exposing the plurality of hooks upon rotation of one of the first and second body portions relative to the other of the first or second body portions; and
translatable actuation means for embedding the exposed plurality of hooks into the wall upon translation of one of the first and second body portions relative to the other of the first or second body portions.

11. The automatic suturing device of claim 10, further comprising a fluid seal between the first and second body portions.

12. The automatic suturing device of claim 9, wherein the body has a low-profile length in an axial direction of the bore to increase a manipulative capability of the instrument through the bore.

13. The automatic suturing device of claim 12, wherein the length of the body in the axial direction of the bore is substantially within a range of 1.5 T to 5 T, where T is a thickness of the wall.

14. The automatic suturing device of claim 9, wherein the means for engaging a portion of the hooks when in the retracted position and for attaching the sutures to a portion of the plurality of hooks comprises an adhering means for adhering the sutures to a portion of the plurality of hooks.

15. The automatic suturing device of claim 14, wherein the adhering means comprises:
the suture holder having a first longitudinal channel for holding the sutures therein;
the suture holder having a second longitudinal channel for holding a glue therein; and
a linking channel for linking at least a portion of the first and second longitudinal channels and corresponding to at least a portion of the plurality of hooks when in the retracted position;
wherein the at least a portion of the plurality of hooks are disposed in the linking channel and in communication with both the sutures and glue in the respective first and second longitudinal channels when in the retracted position to adhere at least a portion of a suture to at least a portion of each of the plurality of hooks.

16. The automatic suturing device of claim 15, wherein the suture holder has an internal bore and the first and second longitudinal channels are disposed on an inner surface of the internal bore.

17. The automatic suturing device of claim 15, wherein the linking channel is disposed on a distal surface of the suture holder.

18. A method for automatically stitching an opening in tissue using the suturing device in claim 1, the method comprising:
inserting a portion of a device into the opening;
extending a plurality of hooks from the device and through the tissue surrounding the opening;
inserting at least a portion of each of the plurality of hooks back into the device, the inserting of each hook occurring first by linear extension of each hook through the tissue, and secondly by rotation and retraction thereof, each hook to return through the tissue;
attaching the at least a portion of each of the plurality of hooks to a suture;
withdrawing the plurality of hooks and attached suture from the tissue surrounding the opening and through the opening;
severing the sutures from the at least portion of each of the plurality of hooks; and
pulling the sutures to close the opening.

19. The method of claim 18, further comprising tying the sutures together after closing the opening.

20. A method for providing access into an interior of a hollow organ for manipulation of an instrument therein, the method comprising:
providing access to the hollow organ;
making an opening in a wall of the hollow organ;
inserting a body of an access device in the opening;
securing the body to the wall;
passing at least a distal portion of an instrument through a bore in the access device to an interior of the hollow organ;
substantially preventing a fluid in the interior of the hollow organ from leaking outside the hollow organ;
removing the access device from the opening; and
automatically closing the hole in the wall of the internal organ upon removal of the access device from the opening,
wherein the automatically closing comprises:
inserting a portion of the access device into the opening;
extending a plurality of hooks from the access device and through the tissue surrounding the opening;
inserting at least a portion of each of the plurality of hooks back into the access device;
attaching the at least a portion of each of the plurality of hooks to a suture;
withdrawing the plurality of hooks and attached suture from the tissue surrounding the opening and though the opening;
severing the sutures from the at least a portion of each of the plurality of hooks; and
pulling the sutures to close the opening.

21. The method of claim 20, further comprising tying the sutures together after closing the opening.

* * * * *